United States Patent [19]
Zambias

[11] Patent Number: 5,874,403
[45] Date of Patent: Feb. 23, 1999

[54] AMINO ACID CONJUGATES OF CYCLOHEXAPEPTIDYL AMINES

[75] Inventor: Robert A. Zambias, Springfield, N.J.

[73] Assignee: Merck & Co., Inc., Rahway, N.J.

[21] Appl. No.: 959,948

[22] Filed: Oct. 15, 1992

[51] Int. Cl.$^6$ .............................. A61K 38/12; C07K 7/50
[52] U.S. Cl. ..................... 514/11; 514/9; 514/2; 530/317; 530/318
[58] Field of Search ................. 514/11, 9, 2; 530/317, 530/318

[56] References Cited

U.S. PATENT DOCUMENTS

| | | | |
|---|---|---|---|
| 4,173,629 | 11/1979 | Dreyfuss et al. | 434/8 |
| 4,287,120 | 9/1981 | Abbott et al. | 514/11 |
| 4,293,485 | 10/1981 | Debono | 530/317 |
| 4,293,489 | 10/1981 | Debono | 530/317 |
| 4,320,054 | 3/1982 | Abbott et al. | 530/317 |
| 4,931,352 | 6/1990 | Fromtling et al. | 435/71.3 |
| 4,968,608 | 11/1990 | Giacobbe et al. | |
| 5,021,341 | 6/1991 | Giacobbe et al. | |
| 5,021,403 | 6/1991 | Sesin et al. | 514/9 |
| 5,166,135 | 11/1992 | Schwartz | 530/317 |
| 5,194,377 | 3/1993 | Schwartz et al. | 530/317 |
| 5,198,421 | 3/1993 | Chen et al. | 530/317 |

FOREIGN PATENT DOCUMENTS

| | | |
|---|---|---|
| 851310 | 8/1977 | Belgium . |
| 859067 | 3/1978 | Belgium . |
| 0486 011A2 | 5/1992 | European Pat. Off. . |

OTHER PUBLICATIONS

U.S. application No. 07/963,332, filed Oct. 19, 1992 by Milton L. Hammond et al.
U.S. application No. 07/936,558, filed Sep. 3, 1992 by F. A. Bouffard et al.
U.S. application No. 07/960,983, filed Oct. 16, 1992 by F. A. Bouffard et al.
U.S. application No. 07/775,773, filed Oct. 17, 1991 by F. A. Bouffard et al.
Kim et al, Antimicrobial Agents and Chemotherapy, vol. 31, (2), pp. 197–201 (Feb. 1987).

*Primary Examiner*—Ponnathapura Achutamurthy
*Assistant Examiner*—T. D. Wessendorf
*Attorney, Agent, or Firm*—Elliott Korsen; Mark R. Daniel

[57] ABSTRACT

Novel amino acid conjugates of cyclohexa-peptidyl amines having the formula

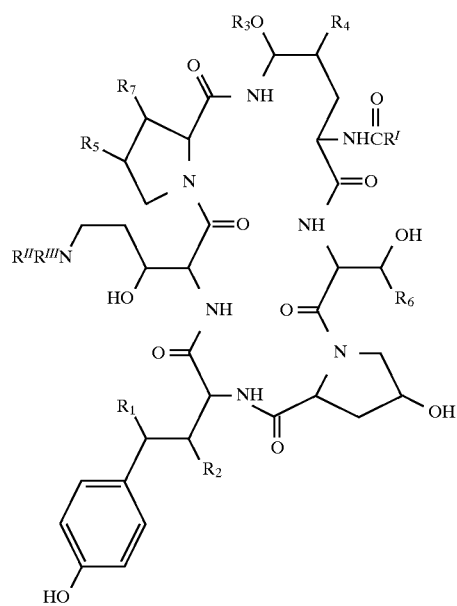

and having antifungal and antiparasital properties are described. The compounds exhibit less acute toxicity than the free amines.

7 Claims, No Drawings

AMINO ACID CONJUGATES OF CYCLOHEXAPEPTIDYL AMINES

The present invention is directed to certain amino acid conjugates of cyclohexapeptidyl amines, to a process for their preparation and their use as a less toxic antifungal agent.

The amino acid conjugates of the present invention may be represented by the formula

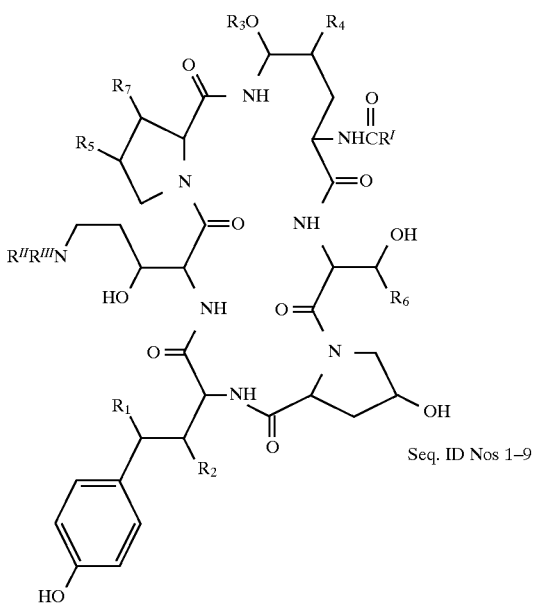

Seq. ID Nos 1–9

In the foregoing and succeeding formulas, $R_1$ is H or OH $R_2$ is H or OH $R_3$ is H, lower alkyl, $C_2$–$C_4$ aminoalkyl, mono- and di-lower alkyl substituted-$C_2$–$C_4$ aminoalkyl, tri-lower-alkyl $C_2$–$C_4$ ammoniumalkyl, wherein each lower alkyl independently is from $C_1$ to $C_4$;

$R_4$ is H or OH $R_5$ is H, $CH_3$ or OH $R_6$ is H or $CH_3$ $R_7$ is H or OH $R^I$ is $C_9$–$C_{21}$ alkyl, $C_9$–$C_{21}$ alkenyl, $C_1$–$C_{10}$ alkoxyphenyl or $C_1$–$C_{10}$ alkoxynaphthyl $R^{II}$ is H, $C_1$–$C_4$ alkyl, $C_3$–$C_4$ alkenyl $R^{III}$ is a conjugate,

where Q is a residue of an amino acid.
provided that at least one of $R_5$ and $R_7$ is OH.

Where the expression "alkyl", "alkenyl" or "alkoxy" is employed, it is intended to include branched as well as straight chain radicals. The term "lower alkyl" refers to C1–4 alkyl.

Included within the scope of the invention are the acid addition salts of the compounds. Pharmaceutically acceptable salts suitable as acid addition salts are those from acids such as hydrochloric, hydrobromic, phosphoric, sulfuric, maleic, citric, acetic, tartaric, succinic, oxalic, malic, glutamic, trifluoroacetic and the like, and include other acids related to the pharmaceutically acceptable salts listed in Journal of Pharmaceutical Science, 66, 2 (1977).

The sequence IDs for the novel compounds of the present invention may be seen in the following table. Since the sequence ID number is assigned for the nuclear variations, and the peptide nuclei would be the same irrespective of the substituents $R^I$, $R^{II}$ or $R^{III}$ or $R_3$, these groups are not listed on the tables.

By "amino acid" is meant to include not only the twenty amino acids commonly found in proteins but also ω-amino acids as well as diamino acids. The acids within the scope of this definition include glycine, alanine, valine, leucine, arginine, serine, threonine, cysteine, methionine, phenylalanine, tyrosine, tryptophan, histidine, proline, glutamic acid, glutamine, aspartic acid, ornithine, lysine, proline, isoleucine, β-alanine, α, ω-diaminapropionic acid, α, ω-diaminobutyric acid, 4-aminobutyric acid, 5-aminopentanoic acid, and 6-aminohexanoic acid.

TABLE

| Nucleus | $R_1$ | $R_2$ | $R_4$ | $R_5$ | $R_6$ | $R_7$ | SEQ ID. |
|---|---|---|---|---|---|---|---|
| I-1 | OH | OH | OH | H | $CH_3$ | OH | 1 |
| I-2 | OH | OH | OH | $CH_3$ | $CH_3$ | OH | 2 |
| I-3 | H | OH | OH | $CH_3$ | H | OH | 3 |
| I-4 | OH | H | OH | $CH_3$ | $CH_3$ | OH | 4 |
| I-5 | H | H | H | $CH_3$ | $CH_3$ | OH | 5 |
| I-6 | OH | OH | OH | OH | $CH_3$ | OH | 6 |
| I-7 | H | OH | OH | H | H | OH | 7 |
| I-8 | H | OH | OH | H | $CH_3$ | OH | 8 |
| I-9 | OH | OH | OH | OH | $CH_3$ | H | 9 |

The starting materials (A) for the preparation of the conjugates are amines which have the same nuclear structure. Thus the sequence IDs for the immediate starting materials are the same i.e., A-1 would have the same groups for $R_1$, $R_2$, $R_4$, $R_5$, $R_6$ and $R_7$, as I-1 and A-2 would have the same groups as I-2 (above), etc. The preparation of the starting materials (A) are hereinafter described and are also more fully described and claimed in copending application Ser. No. 07/936,558, filed Sep. 3, 1992.

When the compounds are free amines, they are soluble in lower alcohols and polar aprotic solvents such as dimethylformamide (DMF) and pyridine. They are insoluble in solvents such as ether and acetonitrile.

The compounds of the present invention are useful as an antibiotic, especially as an antifungal agent or as an anti-protozoal agent. As antifungal agents they are useful for the control of both filamentous fungi and yeasts. They are especially adaptable to be employed for the treatment of mycotic infections in mammals, especially those caused by Candida species such as C. albicans, C. tropicalis and C. pseudotropicalis, and Aspergillus species such as A. fumigatus, A. flavus and A. niger. They are also useful for the treatment and/or inhibition of Pneumocystis carinii pneumonia to which immune compromised patients are especially susceptible as hereinafter described.

The previously noted solubility properties are advantageous for utilization in therapuetic applications, especially in injectible compositions.

The group of compounds particularly outstanding for having the combined properties of effectiveness against difficult fungal species such as Aspergilli, yet exhibiting low acute toxicity to mammals, rendering the compounds especially promising as therapeutic agents are those represented by the following formula

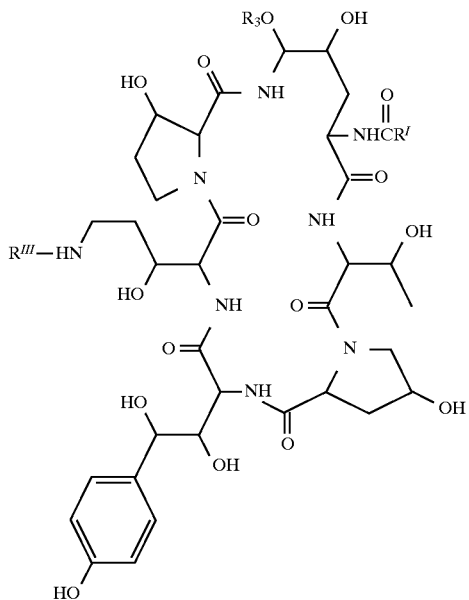

(IA)

wherein $R_3$, $R^I$ and $R^{III}$ are as previously defined.

Most especially preferred are those in which $R_3$ is H, $CH_3$ or $H_2NCH_2CH_2$, and $R^I$ is 9, 11-dimethyltridecyl (DMTD).

The compounds of the present invention are prepared by condensing a protected amino acid (CBz-Q-COX where COX is an activated ester) with a cyclohexapeptidyl amine compound and thereafter removing the protecting group from the amino nitrogen as seen by the following equation:

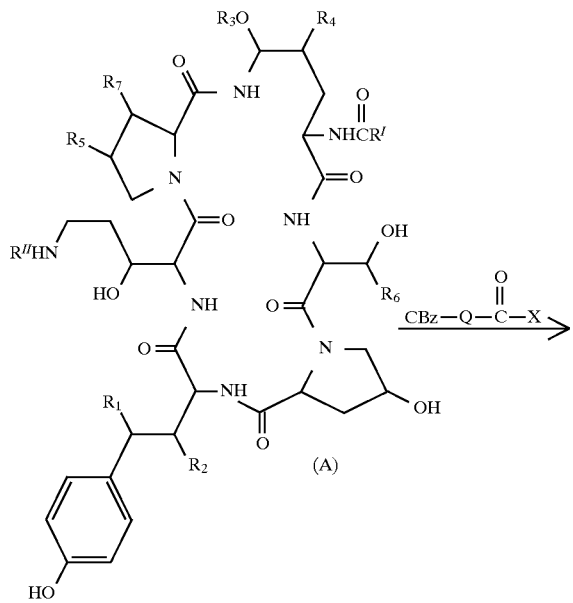

(A)

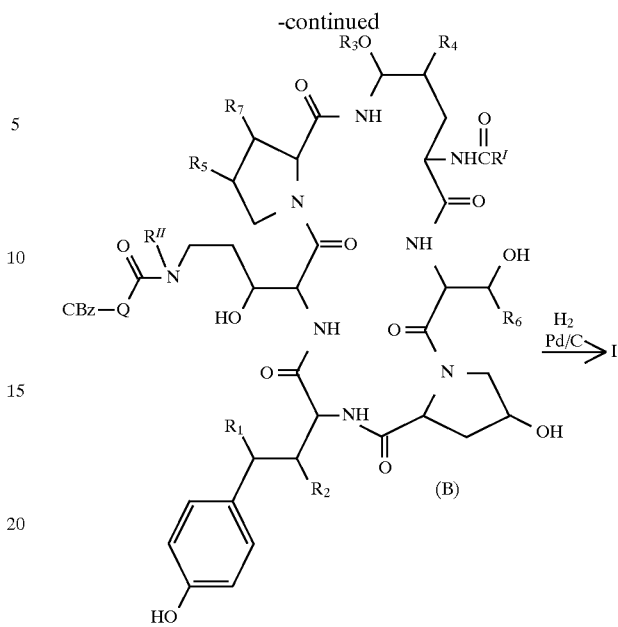

(B)

Generally and preferably, $R^{II}$ is hydrogen.

In carrying out the first step in the preparation of the compounds of the present invention, the amine Compound A preferably as a hydrochloride and carbobenzyloxy(CBz)-protected amino acid are dissolved in dry dimethylformamide (DMF) and to it is added successively diisopropylethylamine, hydroxybenzotriazole hydrate (HOBt) and 1-(3-dimethylaminopropyl)-3-ethylcarbodiimide hydrochloride (ECD) and the resulting mixture stirred under an atmosphere of nitrogen at ambient temperature. The progress of the reaction is monitored by analytical HPLC and when the reaction is determined to be complete, the solution is diluted with the mobile phase for preparative HPLC, and purified by preparative HPLC to obtain the CBz-protected amino acid conjugate of the amine compound (Compound B).

The amine compound starting material, Compound A, is employed as the acid addition salt. The hydrochloride salt is convenient and preferred.

The CBz protected amino acid is employed in two molar equivalents.

The solvent is preferably dimethylformamide (DMF) although other aprotic solvents may be used such as dimethylsulfoxide (DMSO), N-methylpyrrolidone (NMP) and the like. It is essential that the solvent be dry and it is conveniently sieve (13X, 3A) dried.

The tertiary amine is employed in molar equivalent quantities. Diisopropylethyl amine is the preferred amine. Other suitable amines include triethylamine, 4-dimethylaminopyridine (DMAP), pyridine, collidine and the like.

The hydroxybenzotriazole hydrate and 1-(3-dimethylaminopropyl)-3-ethylcarbodiimide hydrochloride are employed in two molar equivalent quantities. Other condensing systems such as dicyclohexylcarbodiimide (DCC) diisopropylcarbodiimide (DIPCDI), benzotriazole-1-yl-oxy-tris-pyrrolidinophosphonium hexafluorophosphate (PyBOP) and benzotriazole-1-yl-oxy-tris-(dimethylamino) phosphonium hexafluorophosphate (BOP) may be employed but the foregoing are preferred.

Alternatively, the activated ester of the CBz protected amino acid may be employed. Such esters include pentafluorophenyl, pentachlorophenyl and p-nitrophenyl.

Analytical HPLC is conveniently carried out on "ZOR-BAX" (DuPont) C18 column (4.5 mm×25 cm) using a $H_2O/CH_3CN$ system as the mobile phase. It is to be understood that as hereinafter employed, both always contain 0.1% trifluoroacetic (TFA) acid) Usually the ratio in the mobile phase is 45/55 $H_2O/CH_3CN$ but may be modified according to the structure of the product being separated. Other conditions are 40° C.; $\lambda$=210 nm; flow rate=1.5 mL/min.

The isolation and purification of the CBz-protected amino acid conjugate is carried out on a preparative HPLC column. Convenient for this purpose is "DELTA-PAK" (Waters Associates) C18, a commercially available 25 mm×50 cm radial compression pack 15 micron particle size 100 Å pore size stationary phase. Several packs may be used in series with water/ acetonitrile as the mobile phase. Other preparative HPLC columns such as the "ZORBAX" (DuPont) preparative column also may be employed.

Generally, when the reaction is complete, the solution is diluted with 70/30 $H_2O/CH_3CN$ and injected directly onto a preparative HPLC column and eluted at 15 mL/min while being monitored at $\lambda$=220 nm. When the solvent and other front running material is eluted, the elution strength (increase $CH_3CN$) of the mobile phase is increased by step gradient. The progress of the separation is monitored by HPLC and the pure fractions are combined and lyophilized to obtain the desired CBz-protected amino acid conjugate.

In carrying out the second step in the preparation of the compounds of the present invention, the CBz-protected amino acid is hydrogenated in methyl alcohol over Pd/C at balloon pressure, monitoring the progress of the reaction with analytical HPLC. When the reaction is determined to be complete, the catalyst is removed and the filtrate injected directly onto a preparative HPLC column, and the desired conjugate product recovered in the eluate. The appropriate fractions are combined and lyophilized to obtain the final product as a TFA salt.

In the hydrogenation an amount of catalyst of about 25% of the weight of substrate is employed. Balloon pressure is convenient. Other low pressure techniques for removing the CBz or other protecting group may be employed.

Both in analytical HPLC and in preparative HPLC, the conditions employed are as in the first step.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

The antifungal properties of the compound may be demonstrated in a representative assay with a compound in which $R_1$, $R_2$, $R_4$ and $R_7$ are —OH, $R_3$ is —$CH_2CH_2NH_2$, $R_5$ is —H, $R_6$ is —$CH_3$, $R^I$ is 9,11-dimethyltridecyl (DMTD) $R^{II}$ is —H and $R^{IV}$ is —COCH ($NH_2$)CH(OH)$CH_3$ (Compound of Example 21, threonine conjugate, aminoalkyl ether). In the assay, Compound I-1a-A was solubilized in 100 percent dimethyl sulfoxide (DMSO) at an initial concentration of 5 mg/ml. Once dissolved, the drug stock was brought to a concentration of 512 μg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 μg/ml. Compounds in the first column were diluted 2-fold across the rows yielding final drug concentrations ranging from 256 μg/ml to 0.12 μg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1-5\times10^4$ colony forming units (CFU)/ml. Aliquots of the suspension (0.075 ml) were inoculated into each well of the microtiter plate resulting in a final cell inoculum of $5-25\times10^3$(CFU)/ml and final drug concentrations ranging from 128 μg/ml to 0.06 μg/ml. Each assay includes one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. However, for *Cryptoccoccus neoformans* strains, SDA plates were inoculated at 48 hours and incubated 48 hours after being spotted on SDA before making minimum fungicidal concentration (MFC) readings. The results were as follows:

| Organism | | MFC μg/mL |
|---|---|---|
| C. albicans | MY 1028 | 0.25 |
| C. albicans | MY 1055 | 0.25 |
| C. albicans | MY 1750 | 0.25 |
| C. guillermondii | MY 1019 | 128. |
| C. parapsilosis | MY 1010 | 0.5 |
| C. pseudotropicalis | MY 1100 | 0.25 |
| C. tropicalis | MY 1012 | 0.25 |
| Cr. neoformans | MY 1051 | 16. |

The compounds also show in vivo effectiveness against fungi which may be demonstrated with the same compound in an assay carried out in the following manner:

Growth from an overnight SDA culture of *Candida albicans* MY 1055 was suspended in sterile saline and the cell concentration determined by hemacytometer count and the cell suspension adjusted to $3.75\times10^5$ cells/ml. Then 0.2 milliliter of this suspension was administered I.V. in the tail vein of mice so that the final inoculum was $7.5\times10^4$ cells/mouse.

The assay then was carried out by administering aqueous solutions of the compound at various concentrations intraperitoneally (I.P.), twice daily (b.i.d.) for four consecutive days to 18 to 20 gram female DBA/2 mice, which previously had been infected with *Candida albicans* in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. The compound, aminoethyl ether of threonine conjugate of I-1 showed greater than 99 percent reduction of recoverable Candida CFUs at 0.375 and 0.09 mg/kg I.P. twice daily for four consecutive days.

The compounds of the present invention may also be useful for inhibiting or alleviating *Pneumocystis carinii* infections in immune compromised patients. The efficacy of the compounds of the present invention for therapeutic or anti-infective purposes may be demonstrated in studies on immunosuppressed rats.

In a representative study, for effectiveness of a compound, Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats are sacrificed to confirm the presence of *Pneumocystis carinii* pneumonia (PCP). Then, five rats (weighing approximately 150 grams) were injected twice daily for four days subcutaneously (sc) with aminoethyl ether of threonine conjugate of I-1 in 0.25 ml of vehicle (distilled water). A vehicle control was also carried out. All animals continued to receive dexamethasone in the drinking water and low protein diet during the treatment period. At the completion of the treatment, all animals were sacrificed, the lungs were removed and processed, and the extent of disease determined by microscopic analysis of stained slides. The results of this study showed that the test compound was effective in reducing *P. carinii* cysts in 5 rats at 0.075 mg/kg.

The conjugates of the present invention unexpectedly show significantly diminished acute toxic response compared with the non-conjugated amine compounds. In a test for acute toxicity in which compounds in 0.2 milliliter of vehicle are injected intravenously into the tail vein of a rat, it required a dose, far above any treatment dose for a lethal effect while the corresponding unconjugated amine was found to have a lethal effect at much lower doses. Thus, Compound I-1-a required 200 mg/kg while unconjugated compound was toxic at 30 mg/kg.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent by weight of Compound I or one of the components. Concentrate compositions suitable for dilutions prior to use may contain 90 percent or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with a lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed.

When the compound is to be employed for control of pneumocystis infections any method may be employed although it may be desirable to directly treat lung and bronchi. In such administration inhalation methods are employed. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound I in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

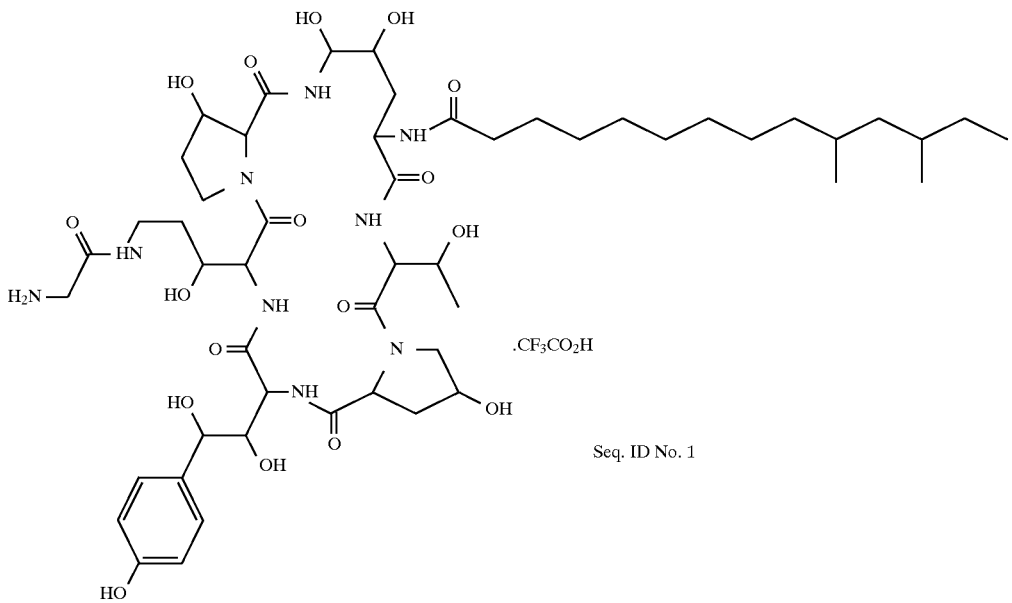

Seq. ID No. 1

Part A — CBz-Protected Glycine Intermediate

To a solution of 210 milligrams (0.20 mmol) of Compound A-1 (where $R_1$–$R_4$=OH, $R_5$=H, $R_6$=$CH_3$; $R_7$=OH; $R'$=DMTD) and 84 milligrams (0.4 mmol) N-CBz-glycine in 2.0 milliliters of sieve-dried DMF was added 34.8 μL (0.20 mmol) of diisopropylamine, followed by 54 milligrams (0.40 mmol) of hydroxybenzotriazole hydrate and finally by 76 milligrams (0.40 mmol) of 1–3-dimethylaminopropyl)-3-ethylcarbodiimide hydrochloride. The reaction mixture was stirred under nitrogen at room temperature and monitored by analytical HPLC (ZORBAX) with 45/55 $H_2O$/$CH_3CN$ as the mobile phase. When the reaction was determined to be complete, the solution was diluted with 2.0 milliliters of 70/30 $H_2O$/$CH_3CN$ and injected directly onto preparative HPLC column (Delta Pak) and eluted at 15 mL/min with 70/30 $H_2O$/$CH_3CN$ with monitoring at λ=220 nm. When all the solvent and other front running material was eluted, the mobile phase strength was increased by step gradient to 55/45 $H_2O$/$CH_3CN$. The pure fractions were combined and lyophilized to obtain 55% yield of CBz glycine conjugate intermediate product of >96.5% purity by analytical HPLC (isocratic elution 40/60 $H_2O$/$CH_3CN$; 1.5 mL/min; 40° C.; λ=210 nm) RT=6.32 min. Mass spectrum (FAB) 1249 (M+Li).

Part B — Glycine Conjugate

The CBz-protected conjugate was hydrogenated in methyl alcohol at a concentration of about 50 mg/mL over 10% Pd on carbon at balloon pressure until the reaction is determined to be complete by HPLC using 45/55 $H_2O$/$CH_3CN$ as the mobile phase. The catalyst was then filtered and the filtrate injected directly onto a DELTA PAK column and eluted with 70/30 $H_2O$/$CH_3CN$ and monitored at λ=220 nm. After the front running material had eluted the mobile phase strength was increased by step gradient and the pure fractions combined and lyophilized to obtain 65 percent yield of product of >96.7% purity by analytical HPLC, elution with 50/50 $H_2O$/$CH_3CN$; 1.5 mL/min; 40° C.; λ=210 nm; RT=6.32 minutes. Mass spectrum (FAB) 1115 (M+Li).

$^1$H NMR (400 MHz; $CD_3OD$) δ 7.12 (d, 2H), 6.75 (d, 2H), 5.20 (d, 1H), 4.96 (d, 1H), 4.35 (q, 1H), 3.45 (m,1H), 2.86 (dd, 1H), 2.44 (m, 1H), 2.23 (t, 2H), 1.21 (d, 3H).

EXAMPLE II
SERINE CONJUGATE

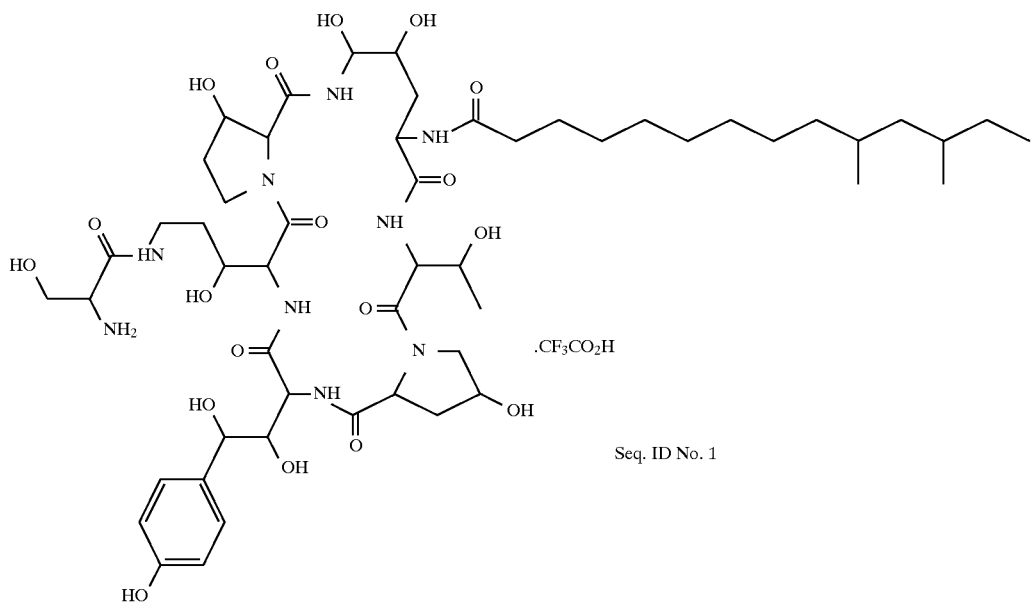

Seq. ID No. 1

Part A — CBz-Serine Intermediate

In an operation similar to that described in Example I, to a solution of 210 milligrams of Compound A-1 (where $R^I$=DMTD) and 96 mg (0.4 mmol) of N-CBz-serine in 2.0 milliliters of sieve-dried DMF was added 34.8 μl (0.20 mmol) of diisopropylamine, followed by 54 milligrams (0.40 mmol) of hydroxybenzotriazole hydrate and then by 76 milligrams (0.40 mmol) of 1-(3-dimethylaminopropyl)-3-ethylcarbodiimide hydrochloride, and the resulting mixture stirred under nitrogen at room temperature while monitoring with analytical HPLC. When the reaction was complete, the mixture was diluted with 2.0 milliliters of 70/30 $H_2O/CH_3CN$ and injected directly onto a preparative HPLC column and then eluted using step gradient elution. The pure fractions were combined and lyophilized to obtain 69 percent yield of CBz-serine intermediate product of >99% by HPLC (50/50 $H_2O/CH_3CN$; 1.5 mL/min; 40° C.; λ=210 nm; RT=9.24 min). Mass Spectrum (FAB) 1279 (M+Li).

Part B — Serine Conjugate

CBz-Serine conjugate was hydrogenated in methyl alcohol at a concentration of about 50 mg/mL over 10% Pd on carbon at balloon pressure until the reaction was complete by HPLC with 45/55 $H_2O/CH_3CN$. The catalyst was filtered and the filtrate injected directly onto a preparative HPLC column and eluted with 70/30 $H_2O/CH_3CN$ and monitored at λ=220 nm. After the front running material had eluted the mobile phase was increased and step gradient elution carried out. Like fractions were combined and lyophilized to obtain 65% yield of product of >99% purity by HPLC: 50/50 $H_2O/CH_3CN$; 1.5 mL/min; 40° C.; λ=210 nm; RT=4.06 min. Mass Spectrum (FAB) 1145 (M+Li).

$^1$H NMR (400 MHz; $CD_3OD$) δ 7.12 (d, 2H), 6.75 (d, 2H), 5.20 (d, 1H), 4.96 (d, 1H), 4.35 (q, 1H), 3.50 (m, 1H), 3.22 (m, 1H), 2.43 (m, 1H), 2.23 (t, 2H), 1.21 (d, 3H).

EXAMPLE III
THREONINE CONJUGATE

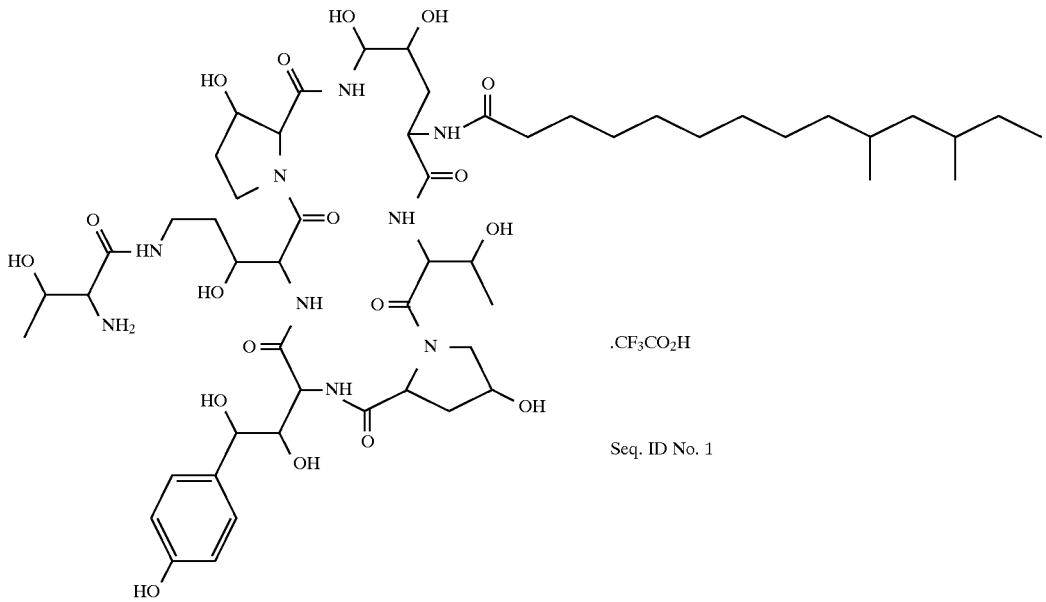

Seq. ID No. 1

Part A. CBz-Threonine Intermediate

In an operation carried out in a manner similar to that described in Examples I and II, 34.8 µL of diisopropylamine, 54 milligrams of hydroxybenzotriazole hydrate and 76 milligrams of 1-(3-methylaminopropyl)-3-ethylcarbodiimide hydrochloride were sequentially added to a solution of 210 milligrams of Compound A-1 (where $R'$=DMTD) and 101 milligrams of CBz-threonine in 2.0 milliliters of sieve-dried DMF and the resulting mixture stirred under nitrogen at ambient temperature while monitoring with analytical HPLC. When the reaction was complete, the mixture was diluted with 70/30 $H_2O/CH_3CN$ and injected directly onto a preparative HPLC column. Appropriate fractions of eluate were combined and lyophilized to obtain a 66 percent yield of product of >97.7 percent purity by analytical HPLC:50/50 $H_2O/CH_3CN$; 1.5 mL/min; 40° C.; λ=210 nm; RT=10.54 min.

Mass spectrum:(FAB) 1293 (M+Li)

Part B — Threonine Conjugate

CBz-Threonine conjugate was hydrogenated in methyl alcohol at a concentration of about 50 mg/mL over 10% Pd on carbon at balloon pressure until reaction was complete. The catalyst was filtered and the filtrate injected onto a preparative HPLC column and eluted with 70/30 $H_2O/CH_3CN$ at λ=220 nm. Like fractions were combined and lyophilized to obtain 65 percent yield of product of >99 percent purity by HPLC: 50/50 $H_2O/CH_3CN$; 1.5 mL/min; 40° C.; λ=210 nm; RT=4.32 min.

Mass sprectrum (FAB) 1158 (M+Li)

$^1$H NMR (400 MHz; $CD_3OD$): δ 7.12 (d, 2H), 6.75 (d, 2H), 5.20 (d, 1H), 4.96 (d, 1H), 4.35 (q, 1H), 3.24 (m, 1H), 2.43 (m, 1H), 2.23 (t, 2H), 1.27 (d, 3H), 1.21 (d, 3H).

In similar operations the following amino acid conjugates were prepared. The mass spectral data for the CBz-intermediate and the mass and proton NMR data for the conjugate products may be seen from the following examples.

EXAMPLE IV
GLUTAMINE CONJUGATE
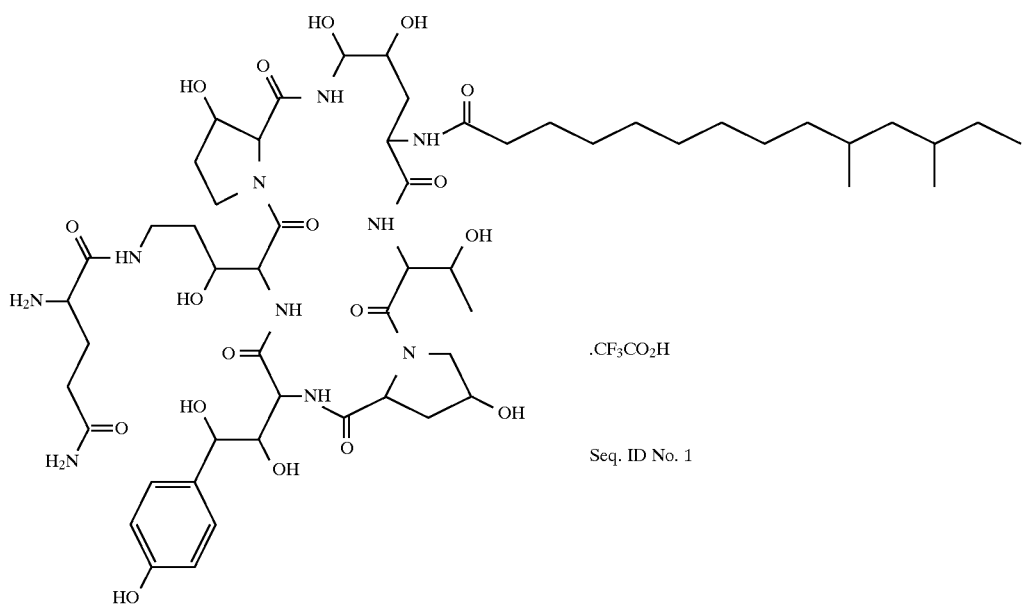
CBz-glutamine Conjugate
  Mass spectrum: (FAB) 1320 (M+Li)
Glutamine Conjugate
  Mass spectrum: (FAB) 1180 (M+Li)
  $^1$H NMR (400 MHz; CD$_3$OD): δ 7.12 (d, 2H), 6.75 (d, 2H), 5.19 (d, 1H), 4.96 (m, 1H), 4.35 (q, 1H), 3.45 (m, 1H), 3.24 (m, 1H), 1.21 (d, 3H).
EXAMPLE V
ARGININE CONJUGATE
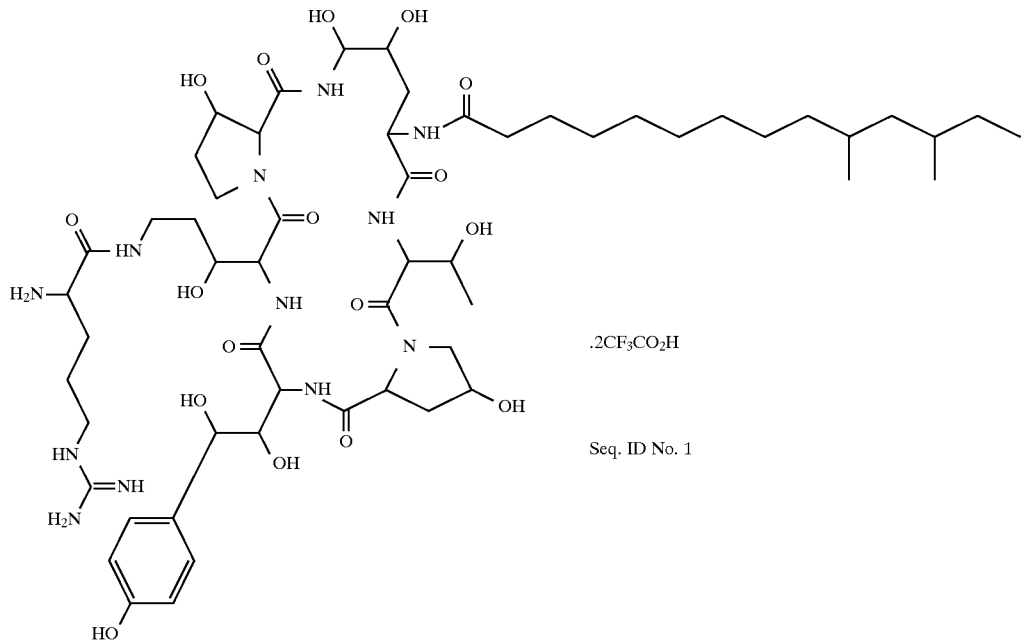
CBz-Arginine Conjugate
  Mass spectrum: (FAB) 1342 (M+1)
Arginine Conjugate
  Mass spectrum: (FAB) 1207 (M+1)

$^1$H NMR (400 MHz; CD$_3$OD): δ 7.12 (d, 2H), 6.75 (d, 2H), 5.20 (d, 1H), 4.96 (m, 1H), 4.35 (q, 1H), 3.22 (t, 2H), 2.43 (m, 1H), 2.23 (t, 2H) 1.21 (d, 3H).
EXAMPLE VI
ALANINE CONJUGATE
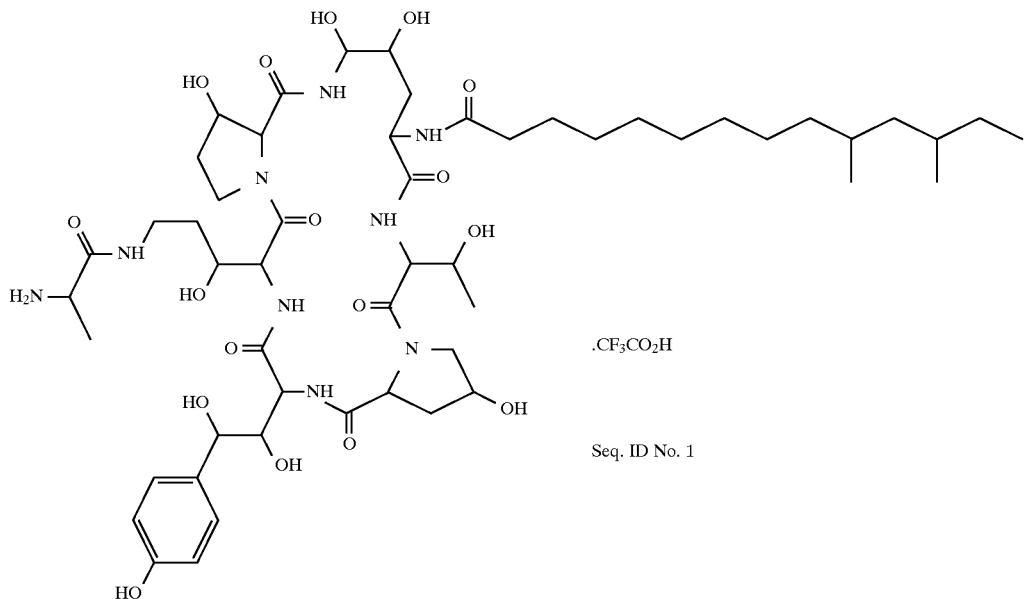
CBz-Alanine Conjugate
Mass spectrum: (FAB) 1262 (M+Li)
Alanine Conjugate
Mass spectrum: (FAB) 1123 (M+1)
$^1$H NMR (400 MHz; CD$_3$OD): δ 7.12 (d, 2H), 6.75 (d, 2H), 5.18 (d, 1H), 4.97 (m, 1H), 4.35 (q, 1H), 3.52 (m, 1H), 3.27 (t, 2H), 2.43 (m, 1H), 2.23 (t, 2H), 1.47 (d, 3H), 1.21 (d, 3H).
EXAMPLE VII
L-Proline Conjugate
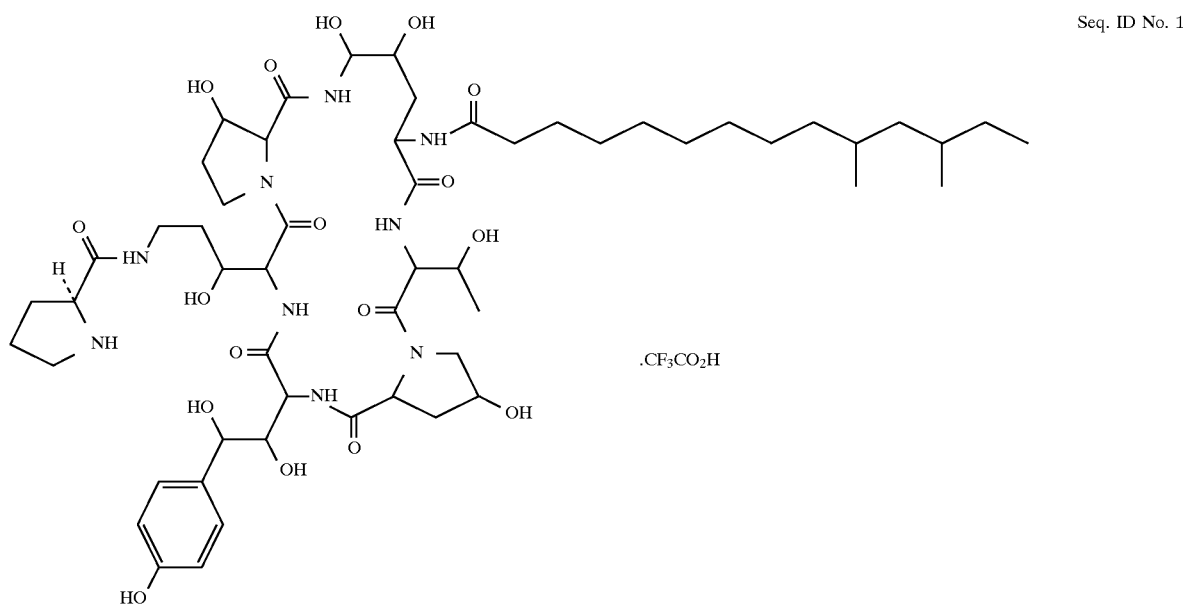

CBz-L-Proline Conjugate
  Mass spectrum: (FAB) 1289 (M+Li)
L-Proline Conjugate
  Mass Spectrum: (FAB) 1148 (M+Li)
  $^1$H NMR (400 MHz; CD$_3$OD) δ 7.12 (d, 2H), 6.75 (d, 2H), 5.20 (m, 1H), 4.96 (dd, 1H), 4.35 (q, 1H), 3.50 (m, 1H), 3.40 (m, 2H), 2.43 (m, 1H), 2.23 (t, 2H), 1.21 (d, 3H).

EXAMPLE VIII

LYSINE CONJUGATE

Di-CBz-Lysine Conjugate

Mass spectrum: (FAB) 1453 (M+Li)

Lysine Conjugate

Mass spectrum: (FAB) 1180 (M+1)

$^1$H NMR (400 MHz; CD$_3$OD) δ 7.12 (d, 2H), 6.75 (d, 2H), 5.18 (d, 1H), 4.97 (d, 1H), 4.45 (q, 1H), 3.44 (m, 1H), 2.95 (m, 1H), 2.43 (m, 1H), 2.23 (t, 2H), 1.21 (d, 3H).

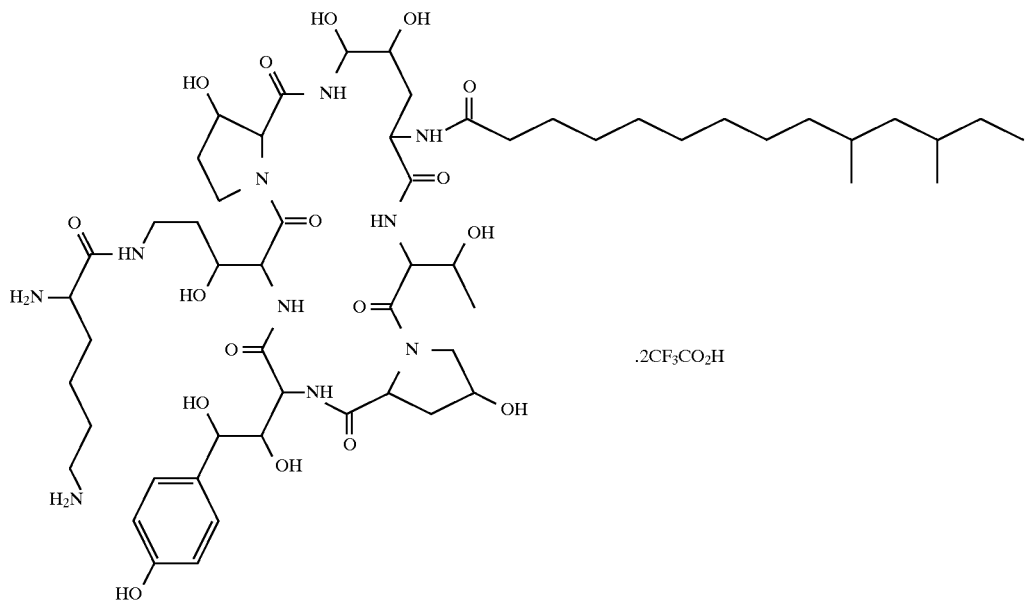

Seq. ID No. 1

.2CF$_3$CO$_2$H

EXAMPLE IX

β-ALANINE CONJUGATE

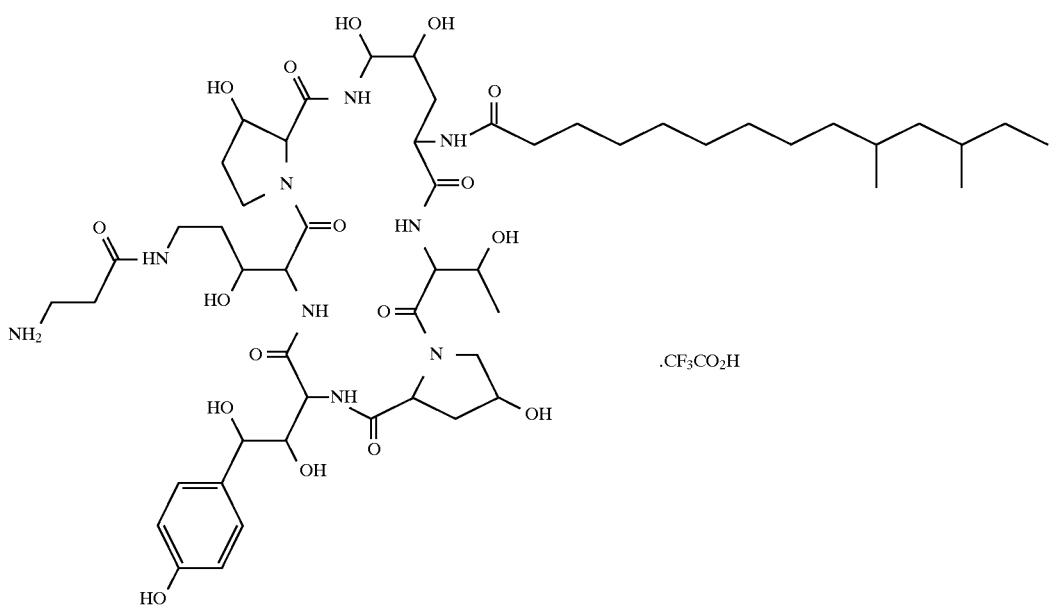

Seq. ID No. 1

.CF$_3$CO$_2$H

CBz-β-Alanine Conjugate
Mass spectrum: (FAB) 1262 (M+Li)
β-Alanine Conjugate
Mass spectrum: (FAB) 1128 (M+Li)
$^1$H NMR (400 MHz; CD$_3$OD): δ 7.12 (d, 2H), 6.75 (d, 2H), 5.18 (d, 1H), 4.97 (d, 1H), 4.45 (dd, 1H), 4.34 (q, 1H), 3.52 (m, 1H), 3.16 (m, 1H), 2.95 (m, 1H), 2.43 (m, 1H), 2.23 (t, 2H), 1.21 (d, 3H).
EXAMPLE X
VALINE CONJUGATE
CBz-Valine Conjugate
Mass spectrum: (FAB) 1290 (M+Li)
Valine Conjugate
Mass spectrum: (FAB) 1156 (M+Li)
$^1$H NMR (400 MHz; CD$_3$OD): δ 7.12 (d, 2H), 6.75 (d, 2H), 5.19 (d, 1H), 4.45 (m, 1H), 4.34 (q, 1H), 3.12 (m, 1H), 2.42 (m, 1H), 2.23 (t, 2H), 1.21 (d, 3H), 1.05 (d, 3H), 1.03 (d, 3H).
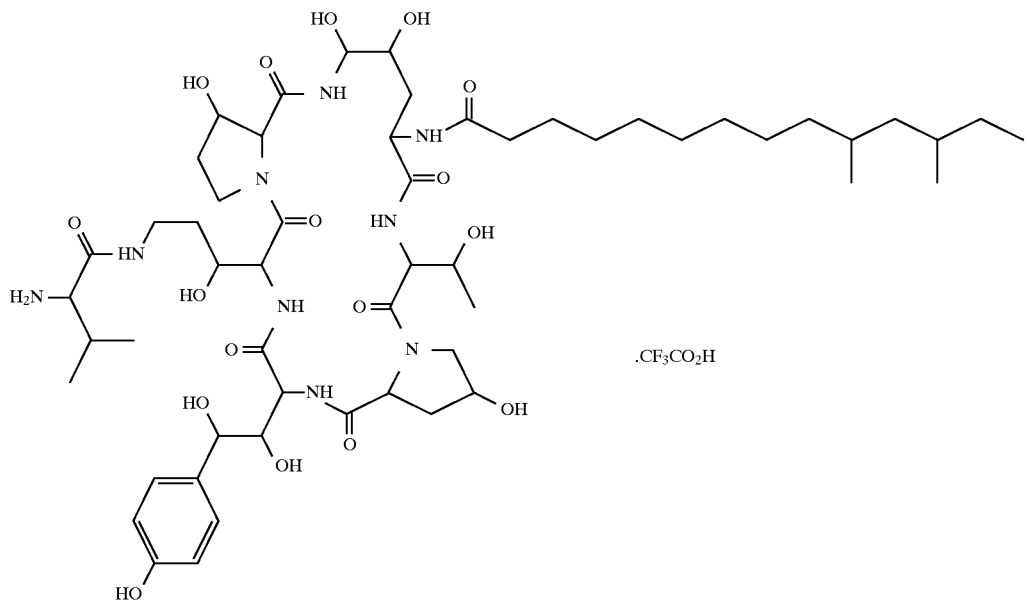
Seq. ID No. 1
EXAMPLE XI
ISOLEUCINE CONJUGATE
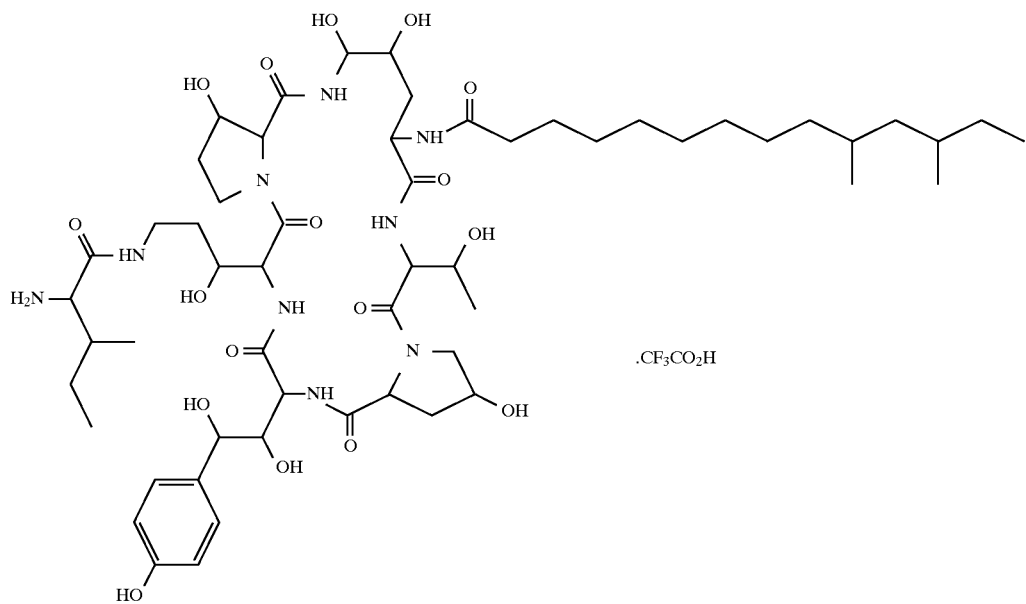
Seq. ID No. 1

CBz-Isoleucine Conjugate

Mass spectrum: (FAB) 1304 (M+Li) Isoleucine Conjugate

Mass spectrum: (FAB) 1170 (M+Li)

$^1$H NMR (400 MHz; CD$_3$OD): δ 7.12 (d, 2H), 6.75 (d, 2H), 5.18 (d, 1H), 4.97 (d, 1H), 4.45 (m, 1H), 4.34 (q, 1H), 3.12 (m, 1H), 2.42 (m, 1H), 2.23 (t, 2H), 1.21 (d, 3H), 1.01 (d, 3H), 0.98 (t, 3H).

EXAMPLE XII

PHENYLALANINE CONJUGATE

CBz-Phenylalanine Conjugate

Mass spectrum: (FAB) 1338 (M+Li)

Phenylalanine Conjugate

Mass spectrum: (FAB) 1204 (M+Li)

$^1$H NMR (400 MHz; CD$_3$OD): δ 7.33 (m, 3H), 7.28 (d, 2H), 7.12 (d, 2H), 6.75 (d, 2H), 5.18 (d, 1H), 4.97 (d, 1H), 4.45 (m, 1H), 4.34 (q, 1H), 3.52 (m, 1H), 3.20 (dd, 1H), 2.42 (m, 1H), 2.21 (t, 2H), 1.21 (d, 3H).

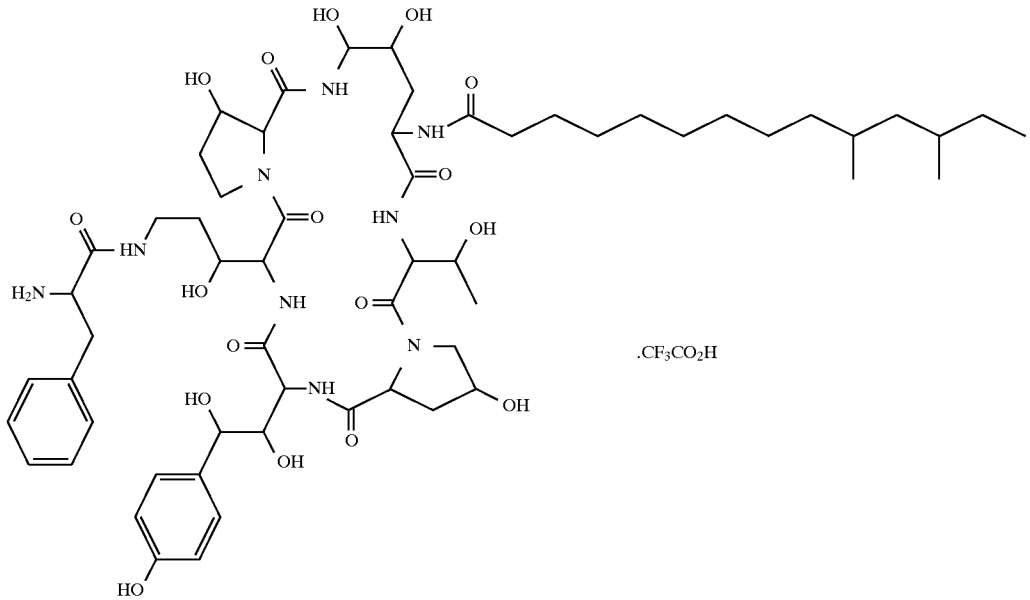

Seq. ID No. 1

EXAMPLE XIII

TYROSINE CONJUGATE

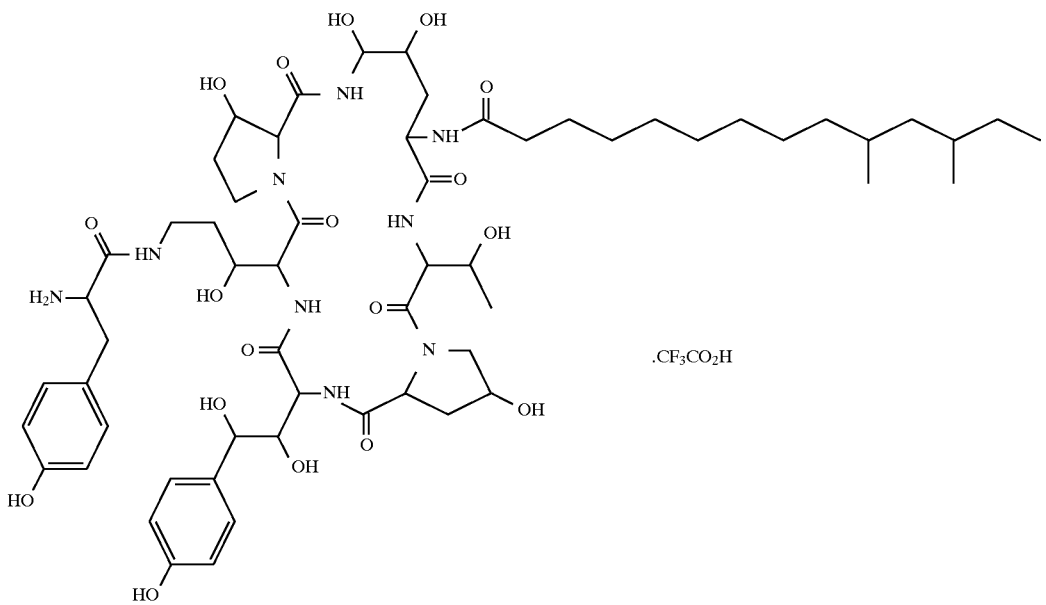

Seq. ID No. 1

CBz-Tyrosine Conjugate
  Mass spectrum: (FAB) 1354 (M+Li)
Tyrosine Conjugate
  Mass spectrum: (FAB) 1220 (M+Li)
  $^1$H NMR (400 MHz; CD$_3$OD) δ 7.12 (d, 2H), 7.08 (d, 2H), 6.78 (d, 2H), 6.75 (d, 2H), 5.18 (d, 1H), 4.95 (d, 1H), 4.34 (q, 1H), 3.52 (m, 1H), 2.92 (m, 1H), 2.42 (m, 1H), 2.21 (t, 2H), 1.21 (d, 3H).
EXAMPLE XIV
LEUCINE CONJUGATE
CBz-Leucine Conjugate
  Mass spectrum: (FAB) 1305 (M+Li)
Leucine Conjugate
  Mass spectrum: (FAB) 1170 (M+Li)
  $^1$H NMR (400 MHz; CD$_3$OD): δ 7.12 (d, 2H), 6.75 (d, 2H), 5.18 (d, 1H), 4.97 (d, 1H), 4.34 (q, 1H), 3.57 (m, 1H), 3.12 (m, 1H), 2.42 (m, 1H), 2.23 (t, 2H), 1.21 (d, 3H), 0.99 (d, 3H), 0.97 (d, 3H).
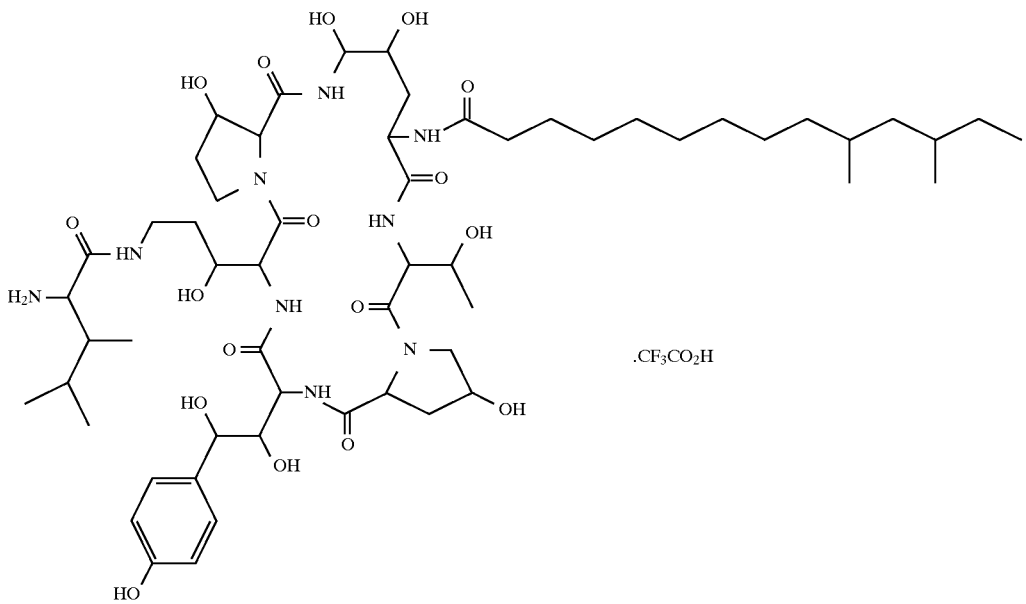
Seq. ID No. 1
EXAMPLE XV
D-Proline Conjugate
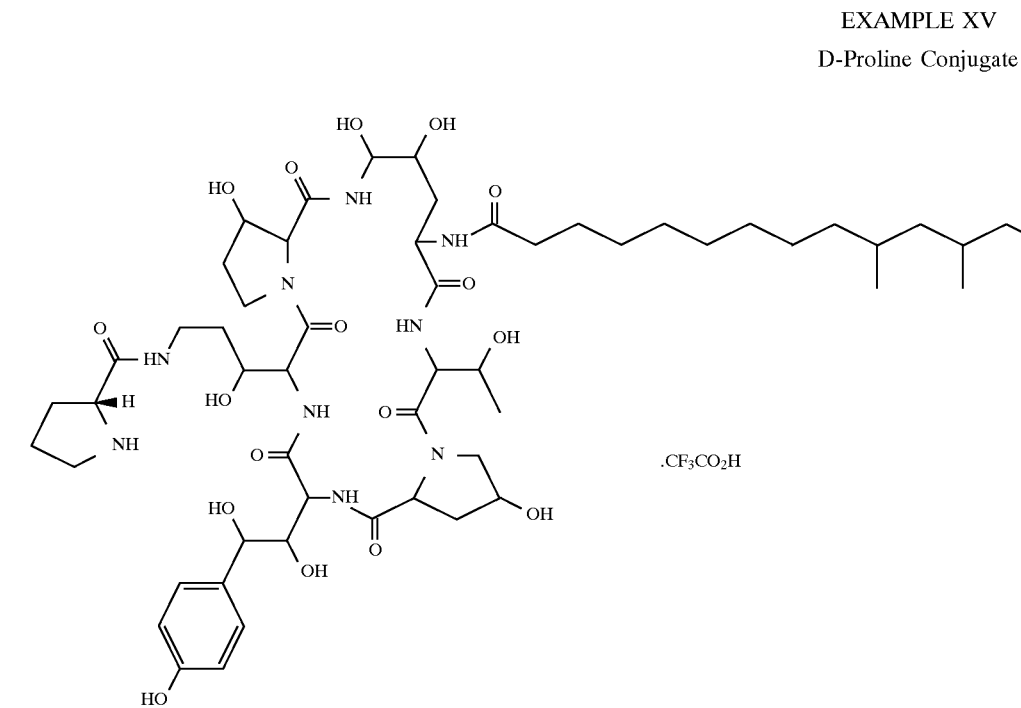
Seq. ID No. 1

CBz-D-Proline Conjugate

Mass spectrum: (FAB) 1289 (M+Li) D-Proline Conjugate

Mass spectrum: (FAB) 1154 (M+Li)

$^1$H NMR (400 MHz; CD$_3$OD): δ 7.12 (d, 2H), 6.75 (d, 2H), 5.22 (m, 1H), 4.96 (dd, 1H), 4.35 (q, 1H), 2.43 (m, 1H), 2.23 (t, 2H), 1.21 (d, 3H).

EXAMPLE XVI

GLUTAMIC ACID CONJUGATE

CBz-γ-Benzyl-Glutamate Conjugate

Mass spectrum: (FAB) 1410 (M+Li)

Glutamic Acid Conjugate

Mass spectrum: (FAB) 1170 (M+Li)

$^1$H NMR (400 MHz; CD$_3$OD): δ 7.12 (d, 2H), 6.75 (d, 2H), 5.20 (dd, 1H), 4.45 (m, 1H), 4.34 (q, 1H), 3.52 (m, 1H), 2.42 (t, 2H), 2.23 (t, 2H), 1.21 (d, 3H).

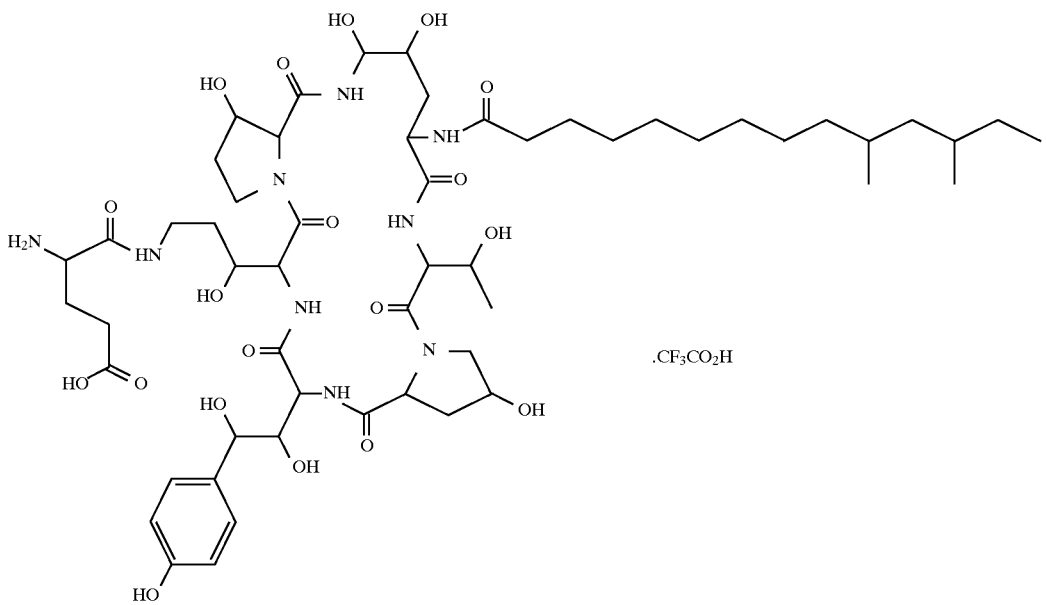

Seq. ID No. 1

EXAMPLE XVII

TRYPTOPHAN CONJUGATE

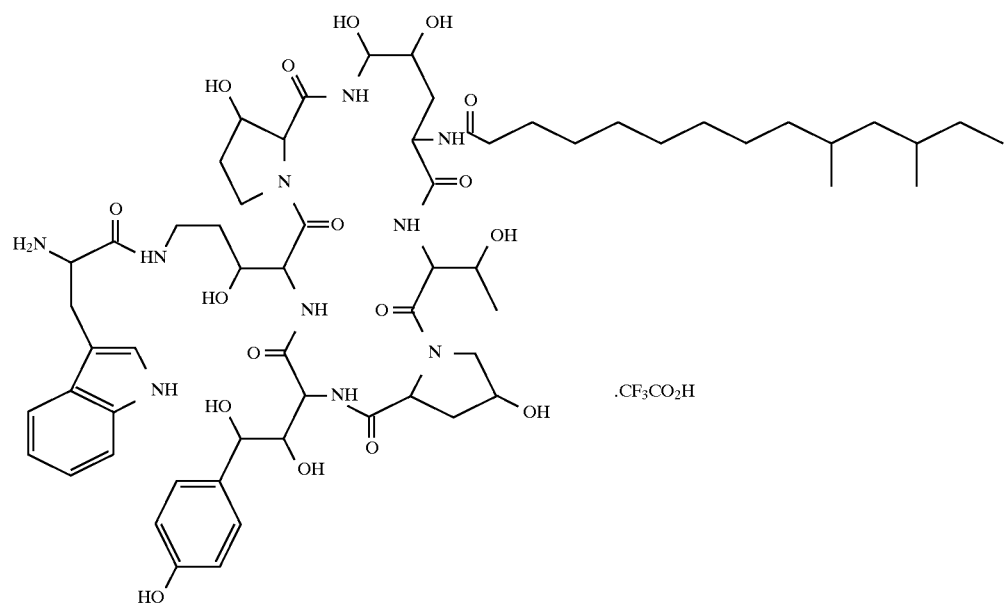

Seq. ID No. 1

CBz-Tryptophan Conjugate

Mass spectrum: (FAB) 1378 (M+Li)

Tryptophan Conjugate

Mass spectrum (FAB) 1244 (M+Li)

$^1$H NMR (400 MHz; CD$_3$OD) δ 7.31 (s, 1H), 6.75 (d, 2H), 5.23 (d, 1H), 4.97 (d, 1H), 4.39 (q, 1H), 3.88 (m, 1H), 2.42 (q, 1H), 3.25 (m, 1H), 2.17 (t, 2H).

EXAMPLE XVIII

HISTIDINE CONJUGATE

CBz-Histidine Conjugate

Mass spectrum: (FAB) 1328 (M+Li)

Histidine Conjugate

Mass spectrum: (FAB) 1194 (M+Li)

$^1$H NMR (400 MHz; CD$_3$OD) δ 7.12 (d, 2H), 6.75 (d, 2H), 5.24 (d, 1H), 4.96 (m, 1H), 4.38 (q, 1H), 4.03 (t, 1H), 3.70 (m, 1H), 3.12 (m, 1H), 2.43 (m, 1H), 2.23 (t, 2H), 1.19 (d, 3H).

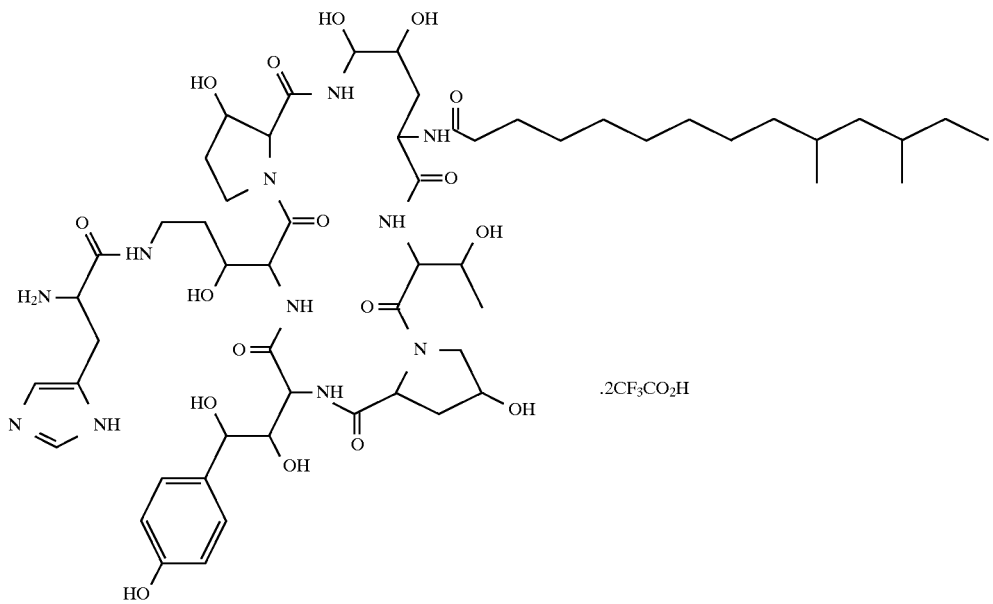

Seq. ID No. 1

EXAMPLE XIX

GLYCINE CONJUGATE MONOMETHYL ETHER

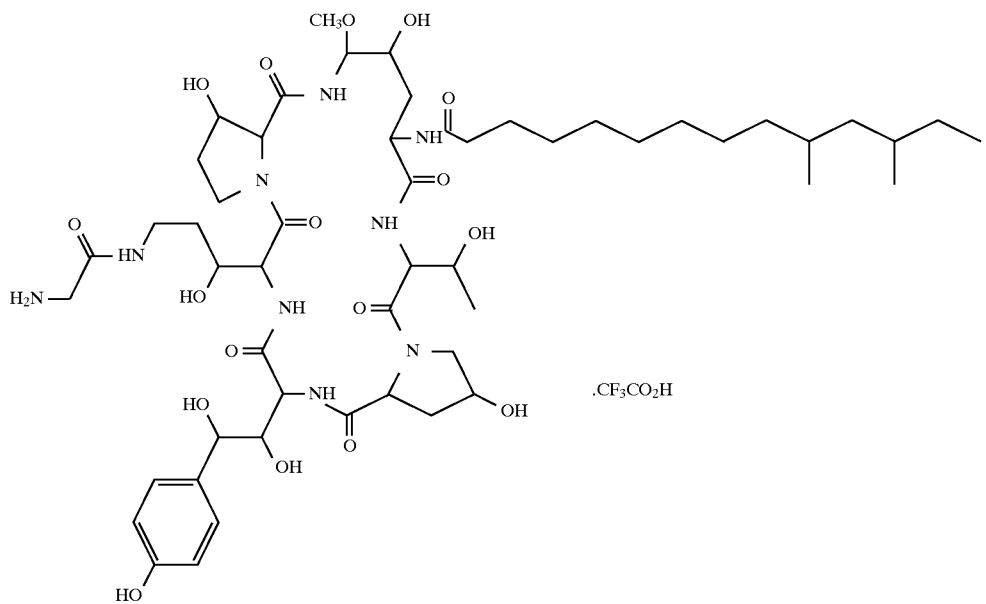

Seq. ID No. 1

CBz-Glycine Conjugate Monomethyl Ether

To a solution of 440 milligrams (0.354 mmol) of CBz-glycine conjugate (prepared as described in Example I) in 20 milliliters methanol was added 164 milligrams (0.708 mmol) of camphorsulfonic acid. The reaction was allowed to continue for 3 hours, then quenched by the addition of 354 microliters of 2M sodium acetate and diluted with 10 milliliters of 50/50 $H_2O/CH_3CN$. The resulting solution was pump injected directly onto a preparative HPLC column (Delta Pak) and eluted at 60 mL/min with 70/30 $H_2O/CH_3CN$. When all the solvent and other front running material was eluted, the elution strength of the mobile phase was increased by step gradient until a final solvent strength of 55/45 was reached. The pure fractions were combined and lyophilized to obtain 285 milligrams (64%) as the TFA salt of purity greater than 94% (HPLC 45/55 $H_2O/CH_3CN$; 1.5 mL/min; 40° C.; $\lambda$210 nm; RT=13.87 min)

Mass spectrum: (FAB) 1262 (M+Li)

Glycine Conjugate Monomethyl Ether

A solution of 185 milligrams of the CBz protected glycine conjugate methyl ether in 4 milliliters of methanol was hydrogenated over 60 mg 10% Pd/C overnight. The reaction mixture was directly injected onto a 25 mm x25 cm. ZORBAX C18 column. Elution was started at 15 mL/min with 80/20 $H_2O/CH_3CN$ and monitored at $\lambda$=220 nm. When the solvent and front running material had eluted, step gradient elution was carried out to a solvent strength of 55/45. Pure fraction were combined and lyophilized to obtain 91 milligrams (50%) of final product of >94% purely as TFA salt. HPLC retention time=4.71 min.

Mass spectrum (FAB) 1128 (M+Li)

$^1$H NMR (400 MHz; $CD_3OD$): $\delta$ 7.12 (d, 2H), 6.75 (d, 2H), 4.98 (d, 1H), 4.44 (dd, 1H), 4.35 (q, 1H), 4.22 (d, 1H), 3.63 (d, 1H), 3.34 (s, 3H), 2.43 (m, 1H), 1.18 (d, 3H).

EXAMPLE XX

GLYCINE CONJUGATE AMINOETHYL ETHER

CBz-Glycine Conjugate Aminoethyl Ether

To a solution of 2.02 grams (20.73 mmol) of ethanolamine in 4 mL dry DMSO was added 0.650 milligram (0.52 mmol) of the glycine conjugate prepared as described in Example I, and the reaction mixture stirred until a complete solution was obtained. Then 130 microliters (0.52 mmol) of 4M HCl in dioxane was added and the reaction allowed to proceed for seven days. At this time it was diluted with 5 milliliters of 50/50 $H_2O/CH_3CN$ and the resulting solution injected directly onto a preparation HPLC column (DELTA PAK) and eluted with 70/30 $H_2O/CH_3CN$ with monitoring at $\lambda$=220 nm. After front running materials were eluted, step gradient elution was carried out to strength 55/45. Pure fractions were combined and lyophilized to obtain 165 milligrams product as TFA salt of >98 percent purity by HPLC.

Mass spectrum: (FAB) 1292 (M+Li).

Glycine Conjugated Aminoethyl Ether

A solution of 158 milligrams of the aminoethyl ether above prepared in 3 milliliters of methanol was hydrogenated over 60 milligrams of 10% Pd/C overnight at balloon pressure. The reaction mixture was then directly pumped onto a preparative HPLC column and eluted at 15 mL/min with 70/30 $H_2O/CH_3CN$. Pure fractions of eluate were combined and lyophilized to obtain 60 milligrams of the conjugate product as the bis TFA salt of >99 percent purity by HPLC (50/50 $H_2O/CH_3CN$; 1.5 mL/min; 40° C.; $\lambda$=210 nm; RT =3.20 min).

Mass spectrum: (FAB) 1157 (M+Li)

$^1$H NMR (400 MHz; $CD_3OD$): $\delta$ 7.12 (d, 2H), 6.75 (d, 2H), 5.23 (d, 1H), 4.96 (d, 1H), 4.48 (dd, 1H), 4.35 (q, 1H), 4.22 (d, 1H), 3.38 (m, 1H), 3.12 (t, 2H), 2.43 (m, 1H), 2.24 (t, 2H), 1.21 (d, 3H).

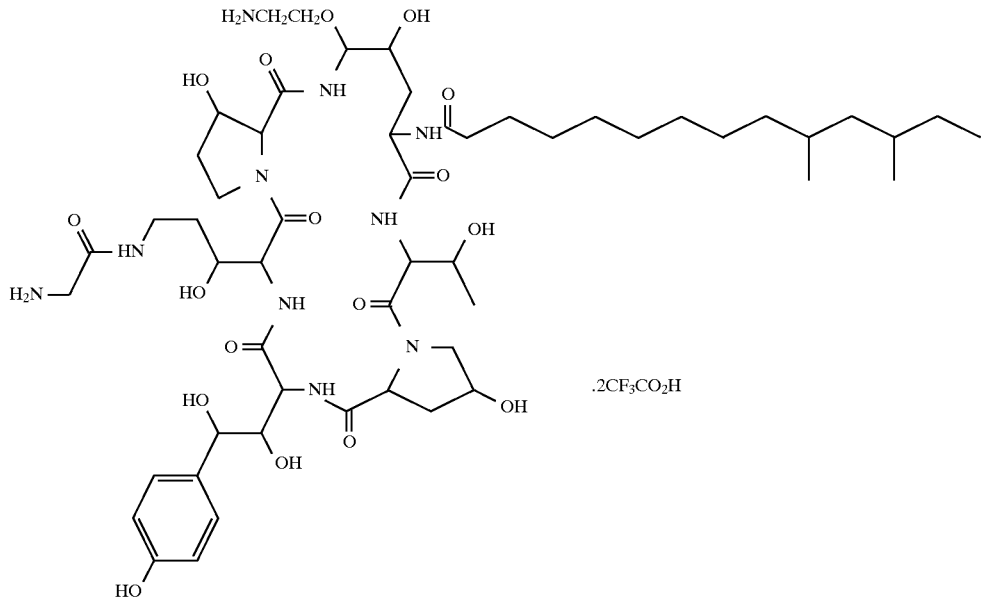

Seq. ID No. 1

EXAMPLE XXI
THREONINE CONJUGATE AMINOETHYL ETHER

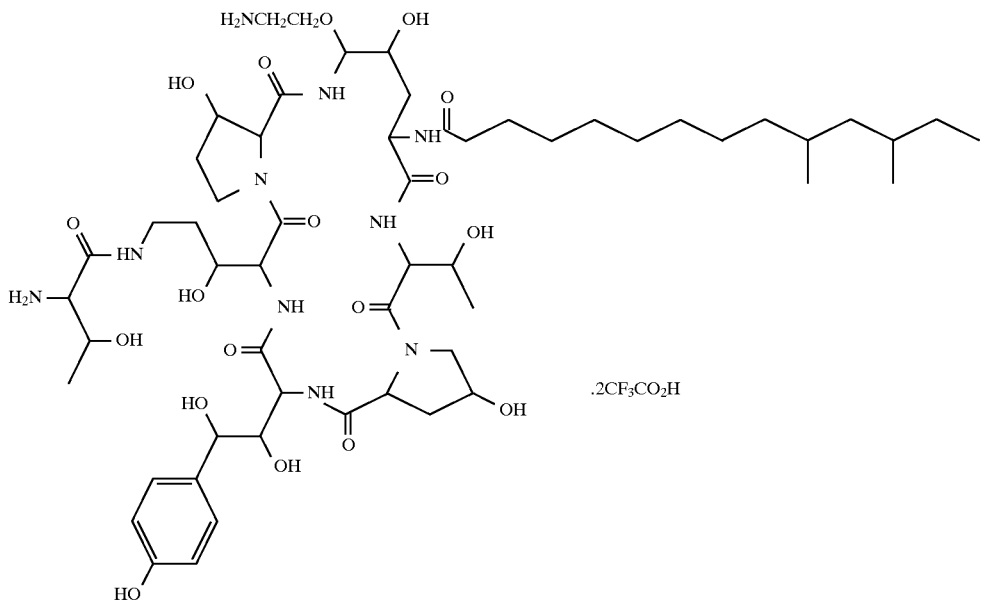

Seq. ID No. 1

.2CF$_3$CO$_2$H

CBz-Threonine Conjugate Aminoethyl Ether

To a solution of 2.42 grams (24.8 mmol) of ethanolamine in 5 mL dry DMSO was added CBz-threonine conjugate prepared as described in Example III. The reaction mixture was stirred until complete solution was obtained; then 155 microliters of 4M HCl in dioxane was added and the reaction allowed to preceed for seven days. At this time it was diluted with 50/50 water/acetonitrile and injected directly onto a preparative HPLC column (DELTA PAK) and monitored at $\lambda$=220 nm. When all the front running material had eluted the strength of the mobile phase was increased step gradiently until final solvent strength of 50/50 was reached. The pure fractions were combined and lyophilized to obtain 265 milligrams of the CBz-threonine conjugate aminoethyl ether product.

Mass spectrum: (FAB) 1336 (M+Li)

Threonine Conjugate Aminoethyl Ether

A solution of 258 milligrams of the ether above prepared in 5 milliliters of methanol was hydrogenated over 52 milligrams of 10 percent Pd/C at balloon pressure. After about 5 hours, another 60 milligrams of 10% Pd/C was added and the hydrogenation allowed to continue overnight. The reaction mixture was filtered, then injected directly onto a ZORBAX column and eluted at 15 mL/min with 70/30 H$_2$O/CH$_3$CN. The pure fractions were combined and lyophilized to obtain 84 milligrams of the desired threonine conjugate aminoethyl ether as the bis TFA salt of greater than 98 percent purity.

Mass spectrum: (FAB) 1201 (M+Li)

$^1$H NMR (400 MHz; CD$_3$OD): $\delta$ 7.12 (d, 2H), 6.75 (d, 2H), 5.23 (d, 1H), 4.35 (q, 1H), 4.22 (d, 1H), 3.45 (m, 1H), 3.12 (t, 2H), 2.43 (m, 1H), 2.24 (t, 2H), 1.27 (d, 3H), 1.21 (d, 3H).

EXAMPLE XXII

In reactions carried out as described in the preceding examples, the following compounds may be prepared from the appropriate amines.

| Nucleus | R$_3$ | R$^I$ | R$^{II}$ | R$^{III}$ | Seq. ID |
|---|---|---|---|---|---|
| 7 | —(CH$_2$)$_4$NH$_2$ | —C$_6$H$_4$OC$_8$H$_{17}$ | H | —COCH$_2$NH$_2$ | 7 |
| 2 | —CH$_2$CH$_2$N(CH$_3$)$_2$ | —C$_6$H$_4$OC$_8$H$_{17}$ | H | —COCH(NH$_2$)CH$_2$OH | 2 |
| 8 | —CH$_3$ | —C$_{10}$H$_6$OC$_8$H$_{17}$ | H | —COCH(NH$_2$)CH$_2$OH | 8 |
| 4 | —H | —C$_6$H$_4$OC$_8$H$_{17}$ | H | —COCH(NH$_2$)(CH$_2$)$_2$CONH$_2$ | 4 |
| 5 | —CH$_2$CH$_2$N(C$_2$H$_5$)$_2$ | —DMTD | H | —COCH(NH$_2$)(CH$_2$)$_2$CONH$_2$ | 5 |
| 6 | —CH$_2$CH$_2$NH$_2$ | —DMTD | H | —COCH(NH$_2$)(CH$_2$)$_3$NH$_2$ | 6 |
| 9 | —CH$_3$ | —C$_6$H$_4$OC$_8$H$_{17}$ | H | —COCH(NH$_2$)CHOHCH$_3$ | 9 |

EXAMPLE XXIII

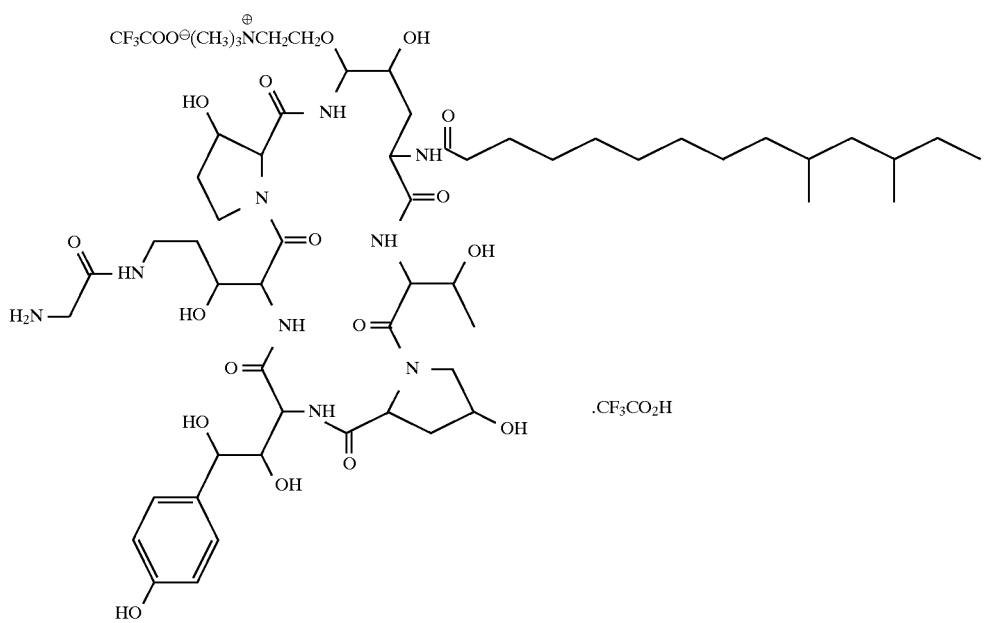

Seq. ID No. 1

To a solution of 46.5 milligrams (42 μmol) of the compounds of Example XX and 100 equivalents of hydroxytrimethyl ammonium chloride is added 20 milligrams (2 equivalents) of camphorsulfonic acid and the resulting mixture stirred at room temperature until HPLC analysis indicated conversion of the starting material. The reaction mixture is then injected directly onto a "ZORBAX" (25 mm×25 cm) C8 column and eluted with 50/50 water/acetonitrile at 8.0 mL/min. Pure fractions as determined by HPLC are pooled and lyophilized to the above monoquaternary bis trifluoroacetate salt, m.w. 1421.

EXAMPLE XXIV

In operations carried out in a manner similar to that described in Example XXIII, the following compounds are prepared:

| Nucleus | $R_3$ | $R^I$ | $R^{II}$ | $R^{III}$ | Seq. ID No. |
|---|---|---|---|---|---|
| 2 | $-CH_2CH_2N^+(CH_3)_3$ | $-(CH_2)_7CH=CH(CH_2)_7CH_3$ | H | $-CO-$[pyrrolidine-NH] | 2 |
| 3 | $-CH_2CH_2N^+(CH_2CH_3)_3$ | DMTD | $CH_3$ | $-COCH_2(NH_2)CH_3$ | 3 |
| 6 | $-CH_2CH_2N^+(CH_3)_3$ | $-C_6H_4OC_4H_{17}$ | $CH_3$ | $-COCH(NH_2)CH_2$-[indole] | 6 |
| 9 | $-CH_2CH_2N^+(CH_2CH_3)_2CH_3$ | $-C_{10}H_6OC_8H_{17}$ | H | $-COCH(NH_2)(CH_2)_4NH_2$ | 9 |
| 1 | $-CH_2CH_2CH_2N^+(CH_3)_3$ | DMTD | $CH_3$ | $-COCH(NH_2)(CH_2)_4NH_2$ | 1 |
| 1 | $-(CH_2)_4N^+(CH_3)_3$ | $-C_6H_4OC_8H_{17}$ | H | $-COCH(NH_2)(CH_2)_3NHCNH_2$ (NH) | 1 |

EXAMPLE XXV
dl-2,3-DIAMINOPROPIONIC ACID CONJUGATE

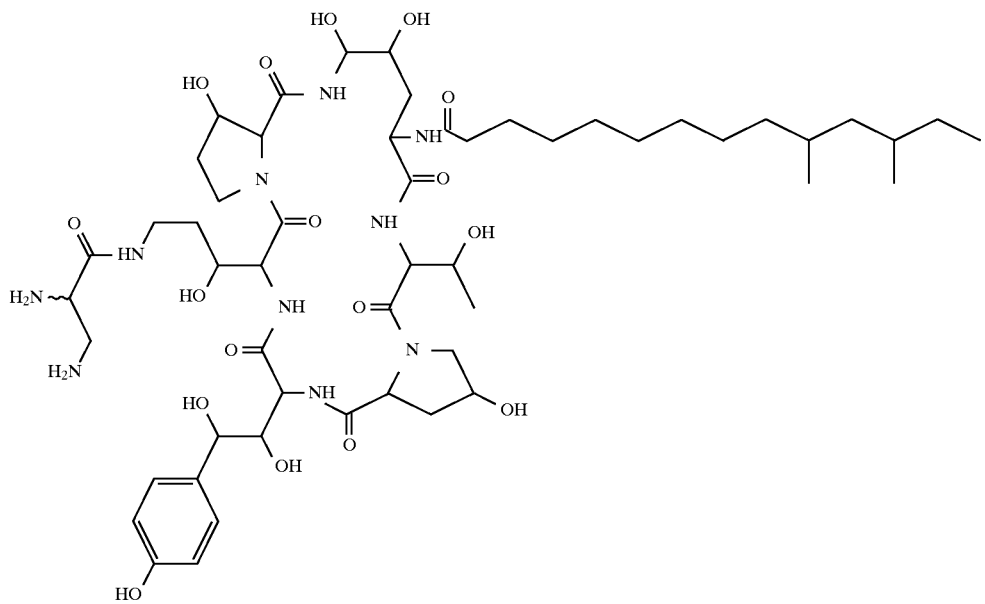

Seq. ID No. 1

CBz-dl-2,3-diaminopropionic Acid Conjugate
  Mass spectrum: (FAB) 1411 (M+Na)
dl-2,3-diaminopropionic Acid Conjugate
  Product of 96.7 percent purity by HPLC: 4.6 mm×25 cm ZORBAX C18; isocratic elution with 45/55 $H_2O/CH_3CN$ both 0.1% TFA; flow rate=1.5 mL/min; temperature=40° C.; λ=210 nm; HPLC retention time=3.22 min.
  Mass Spectrum: (FAB) 1136

EXAMPLE XXVI
ORNITHINE CONJUGATE

Di-CBz-Ornithine Conjugate

Mass spectrum: (FAB) 1439 (M+Li)

Ornithine Conjugate

Mass spectrum: (FAB) 1172 (M+Li)

$^1$H NMR (400 MHz, $CD_3OD$): δ 7.12 (d, 2H), 6.75 (d, 2H), 5.19 (d, 1H), 4.96 (d, 1H), 4.29 (q, 1H), 3.38 (m, 1H), 2.95 (t, 1H), 2.44 (m, 1H), 2.22 (t, 2H), 1.19 (d, 3H).

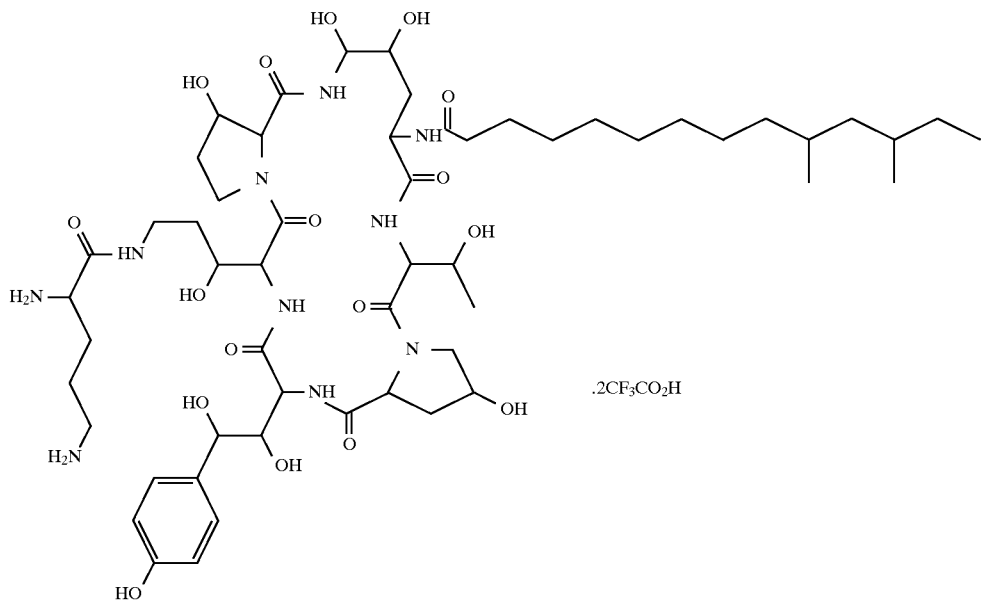

Seq. ID No. 1

.2CF$_3$CO$_2$H

EXAMPLE XXVII
4-AMINOBUTYRIC ACID CONJUGATE

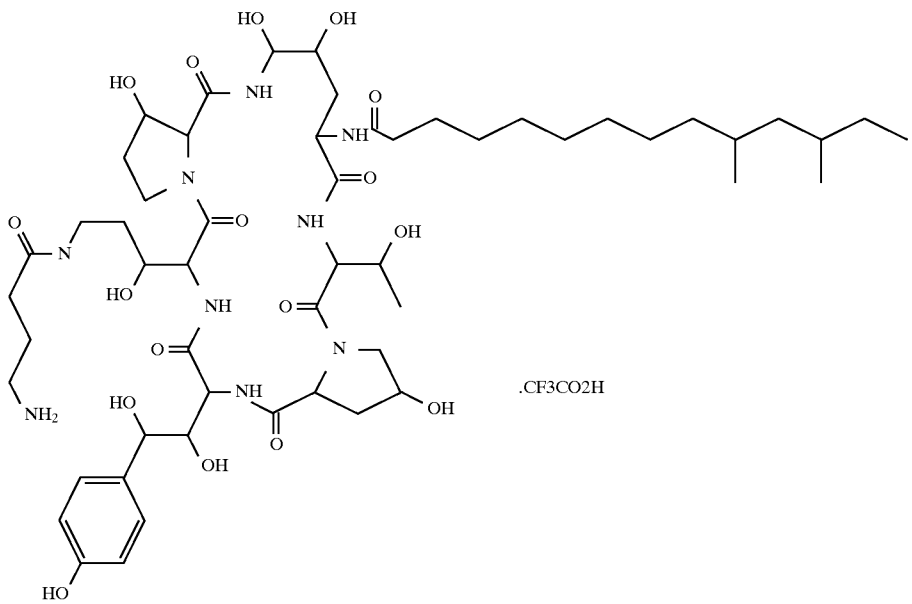

CBz-4-aminobutyric Acid Conjugate
 Mass spectrum: (FAB) 1276 (M+Li)
4-Aminobutyric Acid Conjugate
 Mass spectrum: (FAB) 1143 (M+Li)
 $^1$H NMR (400 MHz, CD$_3$OD): δ 7.12 (d, 2H), 6.75 (d, 2H), 5.20 (d, 1H), 4.96 (d, 1H), 4.27 (q, 1H), 3.35 (m, 1H), 2.95 (t, 1H), 2.41 (m, 1H), 2.25 (t, 2H), 1.20 (d, 3H).

EXAMPLE XXVIII
6-AMINOHEXANOIC ACID CONJUGATE

Product of >99 percent purity by HPLC: 4.6 mm×25 cm Zorbax C18; isocratic elution with 50/50 H$_2$O/CH$_3$CN both 0.1% TFA; flow rate=1.5 mL/min; temperature=40° C.; λ=210 nm; HPLC retention time=11.23 min).
 Mass spectrum: FAB 1305 (M+Li)
6-Aminohexanoic Acid Conjugate
 Product of >96.7 percent purity by HPLC: 4.6 mm×25 cm Zorbax C18; isocratic elution with 5/5 H$_2$O/CH$_3$CN both 0.1% TFA; flow rate=1.5 mL/min; temperature=40° C.; λ=210 nm; HPLC retention time=4.49 min)
 Mass spectrum: (FAB) 1285 (M+Li)

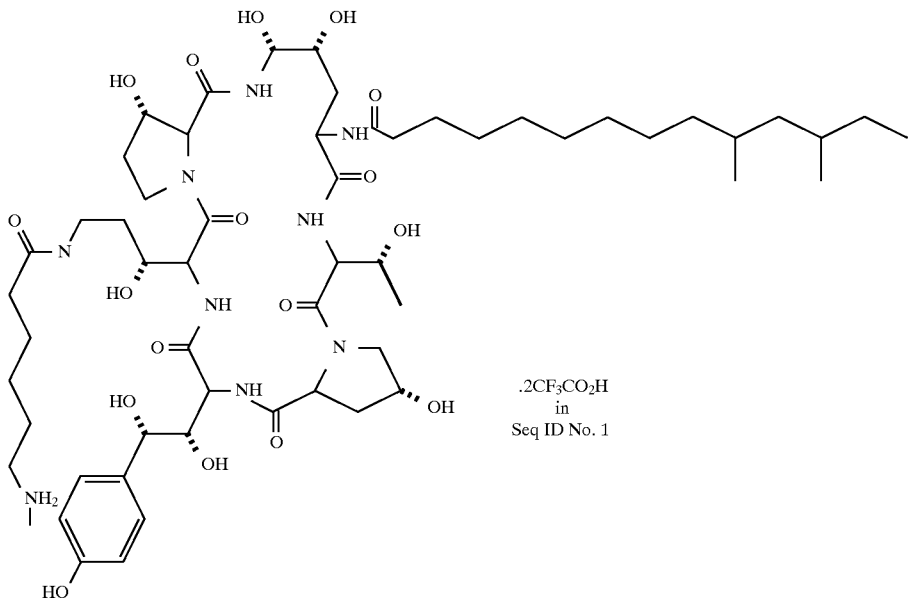

CBz-6-aminohexanoic Acid Conjugate

EXAMPLE XX 1000 hard gelatin capsules each containing 500 mg of Compound of Example 1 are prepared from the following formulation:

| Compound | Grams |
|---|---|
| Compound of Example I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE

An aerosol composition may be prepared having the following formulation:

| | Per Canister |
|---|---|
| Compound of Example IV | 24 mg |
| Lecithin NF Liquid Concentrate | 1.2 mg |
| Trichlorofluoromethane, NF | 4.026 g |
| Dichlorodifluoromethane, NF | 12.15 g |

EXAMPLE 250 milliliters of an injectible solution may be prepared by conventional procedures having the following formulation:

| Dextrose | 12.5 g |
|---|---|
| Water | 250 ml |
| Compound of Example VIII | 400 mg |

The ingredients are blended and thereafter sterilized for use.

Preparation of Starting Materials

The starting amine may be obtained from a natural product (except A-8) or a side chain derivative of a natural product by first subjecting the natural product having an amide group to dehydrating agent to obtain a nitrile. The reaction is preferably carried out under nitrogen with cyanuric chloride in a solvent in the presence or absence of molecular sieves in a solvent such as DMF. The nitrile may then be reduced either by chemical or catalytic reduction. Excess sodium borohydride with cobaltous chloride in an alcoholic solvent is useful. The reaction may be quenched with acid then purified by chromatography. Combined appropriate eluted fractions may then be lyophilized to obtain the amine as TFA or HCl salt as more fully disclosed in copending application Ser. No 07/936,558, filed Sep. 3, 1992.

When $R_3$ is other than H but not containing a quaternary amine nitrogen, the compound prepared in the foregoing paragraph is caused to react with an appropriate alkanolamine in the presence of a strong acid such as camphorsulfonic acid in a solvent such as DMSO or DMF for time sufficient for reaction to take place, then purified HPLC to obtain the aminoalkyl substituted compound.

When $R_3$ is other than H but is an alkyl group bearing a quaternary nitrogen, the compound may be prepared by causing the aminoalkyl substituted compound to react with alkyl iodide in a conventional manner or may be prepared by causing a compound in which $R_3$ is H with an alkanol ammonium compound, (hydroxyalkyl-trialkyl-ammonium compound) e.g. hydroxyethyl trimethyl ammonium chloride in the presence of a strong acid such as camphorsulfonic acid.

The natural products which are used to prepare the above amines may be obtained by cultivating an appropriate organism in a nutrient medium as described in the following references: (a) A-1 may be obtained by cultivating *Zalerion arboricola* ATCC 20868 in a nutrient medium enriched in mannitol as the primary source of carbon as described in U.S. Pat. No. 5,021,341, Jun. 4, 1991; (b) A-2 may be obtained by cultivating *Zalerion arboricola* ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990; (c) A-3 and A-7 may be obtained by cultivating Cryptosporiopsis ATCC 20594 in nutrient medium as described by Pache et al in 13th ICC (1983), PS 4.8/3, Part 115, Abstract No. 10 and PCT WO 82/00587; (d) A-4 and A-5 may be obtained by cultivating *Zalerion arboricola* ATCC 20868 in nutrient medium; (e) A-6 and A-9 may be obtained by cultivating *Z. arboricola* ATCC 74030 in nutrient medium.

Starting amine A-8 for a nucleus in which $R_1$ and $R_5$ are H, $R_2$, $R_4$ and $R_7$ are OH and $R_6$ is $CH_3$ is not from a natural product but may be obtained by adding cyanuric acid to the natural product obtained by cultivating *Z. arboricola* ATCC 20868 as above reference adding said compound to a suspension of cyanuric chloride and molecular sieves in DMF under an atmosphere of nitrogen and stirring conveniently overnight, then after filtering off the sieves, recovering from the filtrate by HPLC eluting with water/acetonitrile containing 0.1% TFA, pooling the appropriate fractions, concentrating and lyophilizing to obtain a compound in which the carboxamide group is replaced with a nitrile. Thereafter, using this as starting material, adding triacetoxyborohydride to a solution of said nitrile in TFA to obtain a nitrile in which the OH on the benzylic carbon of homotyrosine is reduced. The nitrile is then reduced by adding sodium borohydride to a solution of the nitrile in cobaltous chloride in methanol whereupon the amine is formed almost instantaneously. The reaction is quenched by adding 2N HCl and purified by preparative HPLC.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide, and acylating the deacylated cyclopeptide by mixing together with an appropriate active ester $R^ICOX$ to obtain Compound E with the desired acyl group using conventional procedures. Methods are also described in U.S. Pat. Nos. 4,287,120 and 4,293,489.

What is claimed is:

1. A compound having the formula

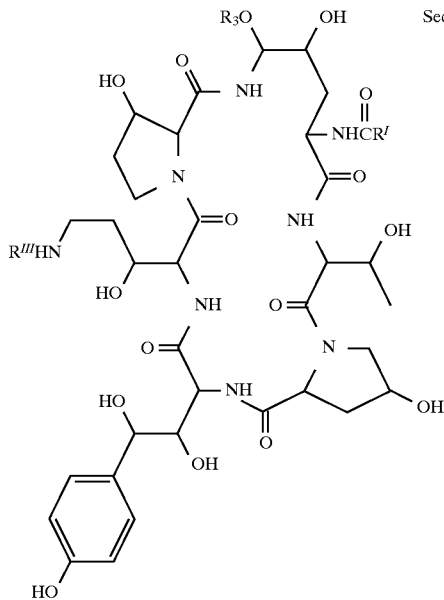

Seq. ID No. 1 wherein

R$_3$ is H, lower alkyl, C$_2$–C$_4$ aminoalkyl, mono- and di-lower alkyl substituted-C$_2$–C$_4$ aminoalkyl, tri lower alkyl C$_2$–C$_4$ ammoniumalkyl, wherein each lower alkyl independently is from C$_1$ to C$_4$;

R$^I$ is C$_9$–C$_{21}$ alkyl, C$_9$–C$_{21}$ alkenyl, C$_1$–C$_{10}$ alkoxyphenyl or C$_1$–C$_{10}$ alkoxynaphthyl R$^{III}$ is a conjugate,

of amino acid where Q is a residue of an amino acid provided that at least one of R$_5$ and R$_7$ is OH.

2. A compound according to claim 1 wherein R$_3$ is OH, R$^I$ is 9,11-dimethyltridecyl and R$^{III}$ is a conjugate of an amino acid selected from the group consisting of

| (a) | threonine | (n) | leucine |
|---|---|---|---|
| (b) | glycine | (o) | glutamic acid |
| (c) | arginine | (p) | tryptophan |
| (d) | serine | (q) | histidine |
| (e) | glutamine | (r) | ornithine |
| (f) | alanine | (s) | α,ω-diaminopropionic |
| (g) | proline | (t) | α,ω-diaminobutyric |
| (h) | lysine | (u) | 4-aminobutyric |
| (i) | β-alanine | (v) | 5-aminopentanoic |
| (j) | valine | (w) | 6-aminohexanoic |
| (k) | isoleucine | | |
| (l) | phenylalanine and | | |
| (m) | tyrosine. | | |

3. A compound according to claim 1 wherein R$_3$ is methyl, R$^I$ is 9, 11-dimethyltridecyl and R$^{III}$ is conjugate of glycine.

4. A compound according to claim 1 wherein R$_3$ is aminoethyl, R$^{III}$ is a conjugate of an amino acid selected from the group consisting of (a) glycine and (b) threonine.

5. An antibiotic composition comprising a therapeutic amount of the compound of claim 1 in admixture with a pharmaceutically acceptable carrier.

6. A composition according to claim 5 in unit dosage form containing from 100 to 200 milligrams of a compound of claim 1.

7. A method of inhibiting mycotic infection comprising administering an antimycotic amount of the compound of claim 1.

* * * * *

UNITED STATES PATENT AND TRADEMARK OFFICE
CERTIFICATE OF CORRECTION

PATENT NO. : 5,874,403
DATED : February 23, 1999
INVENTOR(S) : Robert A. Zambias It is certified that error appears in the above-identified patent and that said Letters Patent is hereby corrected as shown below:

At claim 1, column 48, line 1 should read as follows:

-- of amino acid where Q is a residue of an amino acid. --.

At claim 1, column 48, line 2 should be deleted.

At claim 2, column 48, line 4 should read as follows:

-- 2. A compound according to claim 1 wherein $R_3$ is H, $R^1$ --.

Signed and Sealed this

Seventeenth Day of August, 1999

Attest:

Q. TODD DICKINSON

*Attesting Officer*  Acting Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:1:

Xaa Thr Xaa Xaa Xaa Xaa
    1                     5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

Xaa Thr Xaa Xaa Xaa Xaa
    1                     5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

Xaa Ser Xaa Xaa Xaa Xaa
    1                     5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:4:

Xaa Thr Xaa Xaa Xaa Xaa
    1                     5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular (  i i ) MOLECULE TYPE: peptide ( x i ) SEQUENCE DESCRIPTION: SEQ ID NO:5:

Xaa  Thr  Xaa  Xaa  Xaa  Xaa
1                  5

( 2 ) INFORMATION FOR SEQ ID NO:6:

( i ) SEQUENCE CHARACTERISTICS:
       ( A ) LENGTH: 6 amino acids
       ( B ) TYPE: amino acid
       ( C ) STRANDEDNESS: unknown
       ( D ) TOPOLOGY: circular ( i i ) MOLECULE TYPE: peptide ( x i ) SEQUENCE DESCRIPTION: SEQ ID NO:6:

Xaa  Thr  Xaa  Xaa  Xaa  Xaa
1                  5

( 2 ) INFORMATION FOR SEQ ID NO:7:

( i ) SEQUENCE CHARACTERISTICS:
       ( A ) LENGTH: 6 amino acids
       ( B ) TYPE: amino acid
       ( C ) STRANDEDNESS: unknown
       ( D ) TOPOLOGY: circular ( i i ) MOLECULE TYPE: peptide ( x i ) SEQUENCE DESCRIPTION: SEQ ID NO:7:

Xaa  Ser  Xaa  Xaa  Xaa  Xaa
1                  5

( 2 ) INFORMATION FOR SEQ ID NO:8:

( i ) SEQUENCE CHARACTERISTICS:
       ( A ) LENGTH: 6 amino acids
       ( B ) TYPE: amino acid
       ( C ) STRANDEDNESS: unknown
       ( D ) TOPOLOGY: circular ( i i ) MOLECULE TYPE: peptide ( x i ) SEQUENCE DESCRIPTION: SEQ ID NO:8:

Xaa  Thr  Xaa  Xaa  Xaa  Xaa
1                  5

( 2 ) INFORMATION FOR SEQ ID NO:9:

( i ) SEQUENCE CHARACTERISTICS:
       ( A ) LENGTH: 6 amino acids
       ( B ) TYPE: amino acid
       ( C ) STRANDEDNESS: unknown
       ( D ) TOPOLOGY: circular ( i i ) MOLECULE TYPE: peptide ( x i ) SEQUENCE DESCRIPTION: SEQ ID NO:9:

Xaa  Thr  Xaa  Xaa  Xaa  Xaa
1                  5